US012730108B2

(12) United States Patent
Modiano et al.

(10) Patent No.: US 12,730,108 B2
(45) Date of Patent: Sep. 8, 2026

(54) ARTIFICIAL INTELLIGENCE FOR EARLY CANCER DETECTION

(71) Applicant: Regents of the University of Minnesota, Minneapolis, MN (US)

(72) Inventors: Jaime F. Modiano, Minneapolis, MN (US); Taylor A. DePauw, Minnetonka, MN (US); Ali Khammanivong, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1271 days.

(21) Appl. No.: 17/597,609

(22) PCT Filed: Jul. 15, 2020

(86) PCT No.: PCT/US2020/042196

§ 371 (c)(1),
(2) Date: Jan. 13, 2022

(87) PCT Pub. No.: WO2021/011698

PCT Pub. Date: Jan. 21, 2021

(65) Prior Publication Data

US 2022/0252602 A1 Aug. 11, 2022

Related U.S. Application Data

(60) Provisional application No. 62/874,044, filed on Jul. 15, 2019.

(51) Int. Cl.
*G01N 33/575* (2026.01)
*G16H 50/20* (2018.01)

(52) U.S. Cl.
CPC . *G01N 33/57557* (2026.01); *G01N 33/57585* (2026.01); *G16H 50/20* (2018.01); *G01N 2333/70585* (2013.01); *G01N 2333/70589* (2013.01); *G01N 2333/70596* (2013.01); *G01N 2800/60* (2013.01); *G01N 2800/7014* (2013.01)

(58) Field of Classification Search
CPC ....... G01N 33/57407; G01N 33/57488; G01N 2333/70585; G01N 2333/70589; G01N 2333/70596; G01N 2800/60; G01N 2800/7014; G16H 50/20
See application file for complete search history.

(56) References Cited

U.S. PATENT DOCUMENTS

| | | | | |
|---|---|---|---|---|
| 7,910,315 | B2 | 3/2011 | Modiano et al. | |
| 2014/0148350 | A1* | 5/2014 | Spetzler ............ | G01N 33/6893 436/501 |
| 2015/0152474 | A1 | 6/2015 | Pawlowski et al. | |

OTHER PUBLICATIONS

Xiao Y. A deep learning-based multi-model ensemble method for cancer prediction. Computer Methods and Programs in Biomedicine 153: 1-9. (Year: 2018).*
Boesch M. Flow cytometry: to dump or not to dump. Journal of Immunology 201(7); 1813-1815. (Year: 2018).*
Schick AR. Development and validation of a hemangiosarcoma likelihood prediction model in dogs presenting with spontaneous hemoabdomen: The HELP score. Journal of Veterinary Emergency and Critical Care 29(3): 239-245. (Year: 2019).*
Doan M. Diagnostic potential of imaging flow cytometry. Trends in Biotechnology 36(7): 649-652. (Year: 2018).*
Williams DL. Studies of canine leukocyte antigens: a significant advance in canine immunology. The Veterinary Journal 153: 31-39. (Year: 1997).*
Burinaru TA. Detection of circulating tumor cells using microfluidics. ACS Combinatorial Science 20: 107-126. (Year: 2018).*
Borgatti A. Safe and effective sarcoma therapy through bispecific targeting of EGFR and uPAR. Molecular Cancer Therapeutics 16(5): 956-965. (Year: 2017).*
Moon H. Classification methods for the development of genomic signatures from high-dimensional data. Genome Biology 7: R121, 7 pgs. (Year: 2006).*
Anzar I. NeoMutate: an ensemble machine learning framework for the prediction of somatic mutations in cancer. BMC Biomedical Genomics 12(63): 14 pgs. (Year: 2019).*
"Circulating Tumor Cell Detection for Hemangiosarcoma Diagnosis in Dogs," CTOS Abstract, Nov. 15, 2018, 2 pp.
"Rank—Orange Visual Programming 3 documentation," retrieved from https://orange3.readthedocs.io/projects/orange-visual-programming/en/lat, on Feb. 10, 2022, 4 pp.

(Continued)

*Primary Examiner* — Olivia M. Wise
*Assistant Examiner* — Robert J. Kallal
(74) *Attorney, Agent, or Firm* — Shumaker & Sieffert, P.A.

(57) ABSTRACT

Systems, devices, and techniques are described for characterizing subjects, such as dogs or humans, into risk categories using a blood test. For example, a method includes marking a plurality of cells from a blood sample of a subject with antibodies that recognize a plurality of markers comprising at least two of $\alpha v\beta_3$-integrin, hematopoietic progenitor marker CD34, hematopoietic progenitor marker CD117, hyaluronic acid receptor CD44, or panleukocyte marker CD45 and obtaining, based on expression of the plurality of markers in the plurality of cells, a plurality of data features for the plurality of cells. The method may also include applying a plurality of trained analytical models to a subset of the plurality of data features and generating, based on the trained analytical models, one classification for the blood sample, wherein the classification is selected from at least a high risk of HSA and a low risk of HSA.

14 Claims, 30 Drawing Sheets

(56) References Cited

OTHER PUBLICATIONS

Depauw et al., "Circulating Tumor Associated Cells in Canine Hemangiosarcoma: A Method for Early Detection," Abstract # B22, University of Minnesota, Apr. 2020, 1 pg.
Depauw et al., "Circulating Tumor Cell Detection for Hemangiosarcoma Diagnosis in Dogs," University of Minnesota, retrieved on Jan. 31, 2019, 1 pg.
International Preliminary Report on Patentability from International Application No. PCT/US2020/042196, dated Jan. 27, 2022, 7 pp.
International Search Report and Written Opinion of International Application No. PCT/US2020/042196, dated Sep. 30, 2020, 8 pp.
Lamerato-Kozicki et al., "Canine Hemangiosarcoma Originates from Hematopoietic Precursors with Potential for Endothelial Differentiation," Experimental Hematology, vol. 34, No. 7, Jul. 2006, pp. 870-878.
Modiano et al., "Abstract 4592: Early Detection for Strategic Prevention of a Terminal Canine Cancer: A Model to Reduce the Impact of Cancer in our Society," American Association for Cancer Research, Aug. 15, 2020, 4 pp.
Sarver et al., "Increased Risk of Cancer in Dogs and Humans: A Consequence of Recent Extension of Lifespan Beyond Evolutionarily Determined Limitations?," Aging and Cancer, vol. 3, No. 254, Feb. 2022, pp. 3-19.

* cited by examiner

Predicted

| Actual | HSA | Healthy | Other cancer | Presumably healthy | Splenic non-neoplastic | Σ |
|---|---|---|---|---|---|---|
| HSA | 100.0 % | 0.0 % | 0.0 % | 0.0 % | 0.0 % | 18 |
| Healthy | 0.0 % | 97.5 % | 0.0 % | 0.0 % | 2.5 % | 40 |
| Other cancer | 0.0 % | 0.0 % | 95.8 % | 0.0 % | 4.2 % | 24 |
| Presumably healthy | 8.8 % | 45.1 % | 22.0 % | 0.0 % | 24.2 % | 182 |
| Splenic non-neoplastic | 0.0 % | 0.0 % | 0.0 % | 0.0 % | 100.0 % | 17 |
| Σ | 34 | 121 | 63 | 0 | 63 | 281 |

FIG. 4F

Time Horizon to Diagnosis

Proportion Converting 1.00
0.90
0.80
0.70
0.60
0.50
0.40
0.30
0.20
0.10
0.00

0 100 200 300 400 500 600 700

Time from Test to Diagnosis (Days)

Shine On-1 training set
(LDA-transformed 42-Feature)

Shine On 1 training set + dogs with early diagnosis
(LDA-transformed 42-Feature)

$\alpha_v\beta_3$-integrin$^+$ cells from the CD34/c-Kit/$\alpha_v\beta_3$-integrin staining condition (59 HSA-associated cells/100,000 WBCs)

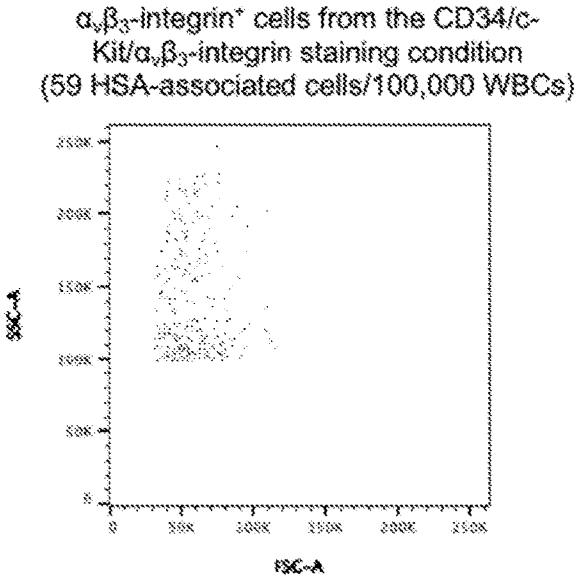

FIG. 21A

CD44$^+$/$\alpha_v\beta_3$-integrin$^+$ cells (44 HSA-associated cells/100,000 WBCs)

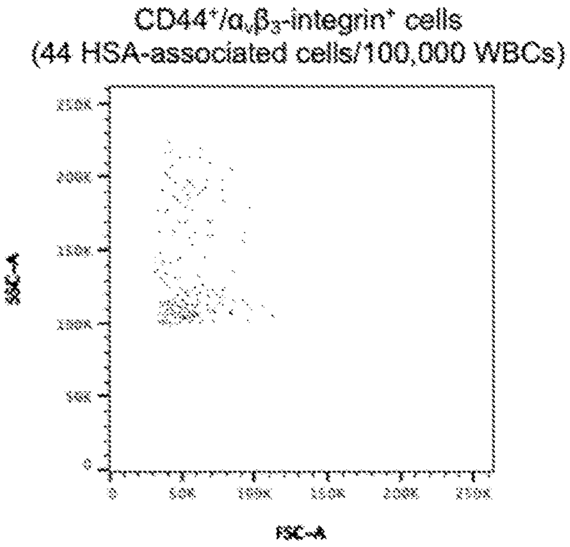

FIG. 21B $\alpha_v\beta_3$-integrin$^+$ cells from the CD34/c-Kit/$\alpha_v\beta_3$-integrin staining condition (0.5 HSA-associated cells/100,000 WBCs)

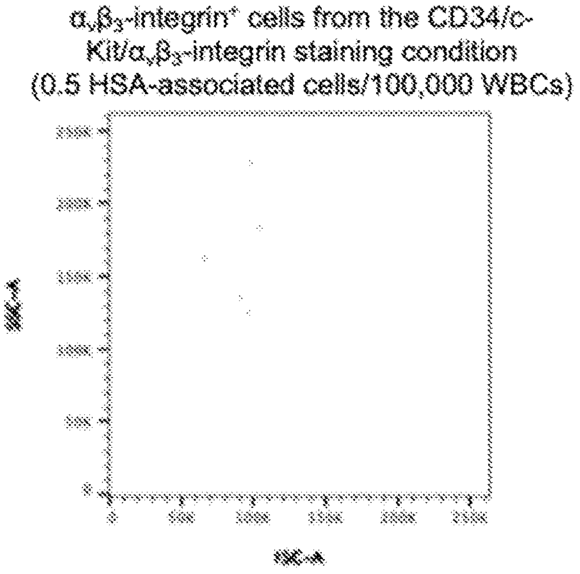

FIG. 21C

CD44$^+$/$\alpha_v\beta_3$-integrin$^+$ cells (0.1 HSA-associated cells/100,000 WBCs)

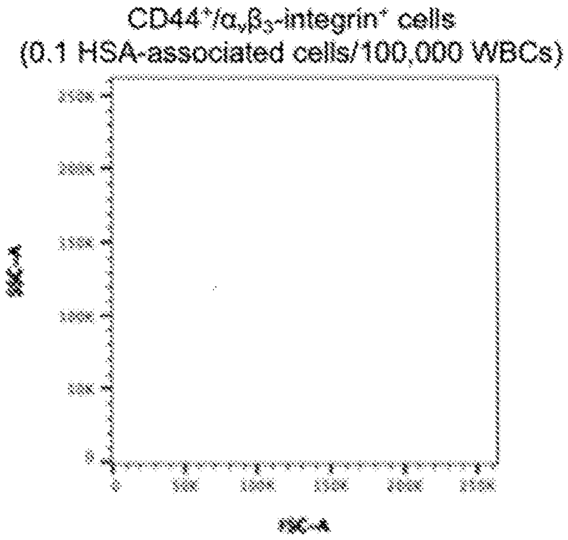

FIG. 21D

ARTIFICIAL INTELLIGENCE FOR EARLY CANCER DETECTION

This application is a National Stage application under 35 U.S.C. § 371 of PCT Application No. PCT/US2020/042196, entitled "ARTIFICIAL INTELLIGENCE FOR EARLY CANCER DETECTION" and filed on Jul. 15, 2020, which claims the benefit of U.S. Provisional Patent Application No. 62/874,044, titled "ARTIFICIAL INTELLIGENCE FOR EARLY CANCER DETECTION" and filed Jul. 15, 2019. The entire contents of application nos. PCT/US2020/042196 and 62/874,044 are incorporated herein by reference.

BACKGROUND

Hemangiosarcoma (HSA) is a common malignancy in dogs. It is an invasive and highly metastatic sarcoma that arises from blood vessel-forming cells. HSA is one type of cancer that can affect dogs, where it is estimated that around 50 percent of dogs over the age of 10 years will develop some type of cancer. HSA does not cause severe clinical signs, such as pain or obvious symptoms, until late states of disease progression. This lack of clinical signs results in difficult diagnoses until late onset and emergency surgery. Once the disease is found, there is no cure for HSA, and HSA is a rapidly fatal disease.

SUMMARY

This disclosure describes systems, devices, and techniques for characterizing subjects, such as dogs, humans, or other animals, into risk categories using a blood test. As described herein, HSA associated cells can be obtained from a blood sample, labeled with one or more specific antibodies, and analyzed using flow cytometry to identify data features of the analyzed cells. A combination of parameters, or data features, may enable a system to characterize, or classify, the subjects into the appropriate risk categories. The risk categories, or classifications, may be used to identify the likelihood that the subject has a certain cancer, such as HSA or a related or another type of cancer such as angiosarcoma.

For example, a system may obtain characteristics associated with a blood sample of a subject, such as data features derived from flow cytometric measurements. The flow cytometric measurements may be obtained from nucleated cells suspended with fluorescently labeled antibodies in different combinations of $\alpha_v\beta_3$-integrin (CD51/CD61), CD5, CD11b, CD22, CD34, CD44, CD45, c-kit, and/or live/dead stain. Other markers may also be used as described herein. The addition of each of these fluorescently labeled antibodies may allow different populations of cells from being distinguished from each other.

The system may then apply a plurality of trained analytical models (e.g., different machine learning algorithms) to at least some of the data features for the blood sample. Each of the trained analytical models may classify the blood sample as being indicative of the subject being healthy or having a certain condition. For example, each of the trained analytical models may classify the blood sample as being indicative of a healthy subject, HSA, non-malignant vascular pathology such as splenic hematoma, or a cancer other than HSA. If a majority of the trained analytical models arrive at the same classification of the blood sample, the system may apply that same classification to the blood sample. If the classifications determined by the group of trained analytical models do not converge, the system may determine that the classification for the blood sample is inconclusive.

In some examples, the system may select the analytical models from a larger pool of different types of initial analytical models which are scored using all or some of the data features for a plurality of subjects. The system may then train the selected analytical models using all or some of the data features for a plurality of subjects. In some examples, the system may continue to train the trained analytical models using blood samples that are validated for each classification, such as confirmed tissue biopsies corresponding to already classified blood samples.

In one example, a method includes obtaining a plurality of cells from a blood sample of a subject, the plurality of cells comprising at least one of circulating tumor cells or circulating tumor-associated cells; marking the plurality of cells with antibodies that recognize a plurality of markers comprising at least two of $\alpha_v\beta_3$-integrin, hematopoietic progenitor marker CD34, hematopoietic progenitor marker CD117, hyaluronic acid receptor CD44, or panleukocyte marker CD45; obtaining, based on expression of the plurality of markers in the plurality of cells, a plurality of data features for the plurality of cells from the blood sample of the subject; applying a plurality of trained analytical models to at least a respective subset of the plurality of data features for the plurality of cells from the blood sample of the subject; and generating, based on the application of the plurality of trained analytical models to at least the respective subset of the plurality of data features, one classification for the blood sample, wherein the classification is selected from a plurality of classification options comprising at least high risk of HSA classification and a low risk of HSA classification.

In another example, a system includes a data repository configured to store a plurality of data features from flow cytometric measurements for a blood sample from a subject and processing circuitry configured to receive the plurality of data features for the blood sample of the subject, execute a prediction engine configured to apply a plurality of trained analytical models to at least a respective subset of the plurality of data features for the blood sample of the subject to compute, for each trained analytical model of the plurality of trained analytical models, one classification for the blood sample, wherein the classification is selected from a plurality of classification options comprising at least a HSA classification and a healthy classification, determine that a threshold quantity of trained analytical models resulted in a same one classification for the blood sample, and responsive to determining that the threshold quantity of trained analytical models of the plurality of analytical models resulted in the same one classification for the blood sample, output the same one classification as a final classification for the blood sample from the subject.

In another example, a method includes storing, by a data repository, a plurality of data features from flow cytometric measurements for a blood sample from a subject, receiving, by processing circuitry, the plurality of data features for the blood sample of the subject, executing, by the processing circuitry, a prediction engine configured to apply a plurality of trained analytical models to at least a respective subset of the plurality of data features for the blood sample of the subject to compute, for each trained analytical model of the plurality of trained analytical models, one classification for the blood sample, wherein the classification is selected from a plurality of classification options comprising at least a HSA classification and a healthy classification, determining, by the processing circuitry, that a threshold quantity of trained analytical models resulted in a same one classification for the blood sample, and responsive to determining that the threshold quantity of trained analytical models of the plurality of analytical models resulted in the same one classification for the blood sample, outputting, by the processing circuitry, the same one classification as a final classification for the blood sample from the subject The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 4E and 4F illustrate results of the analytical models shown in FIG. 4D.

FIGS. 21A, 21B, 21C, and 21D are graphs illustrating a screening test for HSA associated cells before and after preventative treatment.

DETAILED DESCRIPTION

Figure 1A:
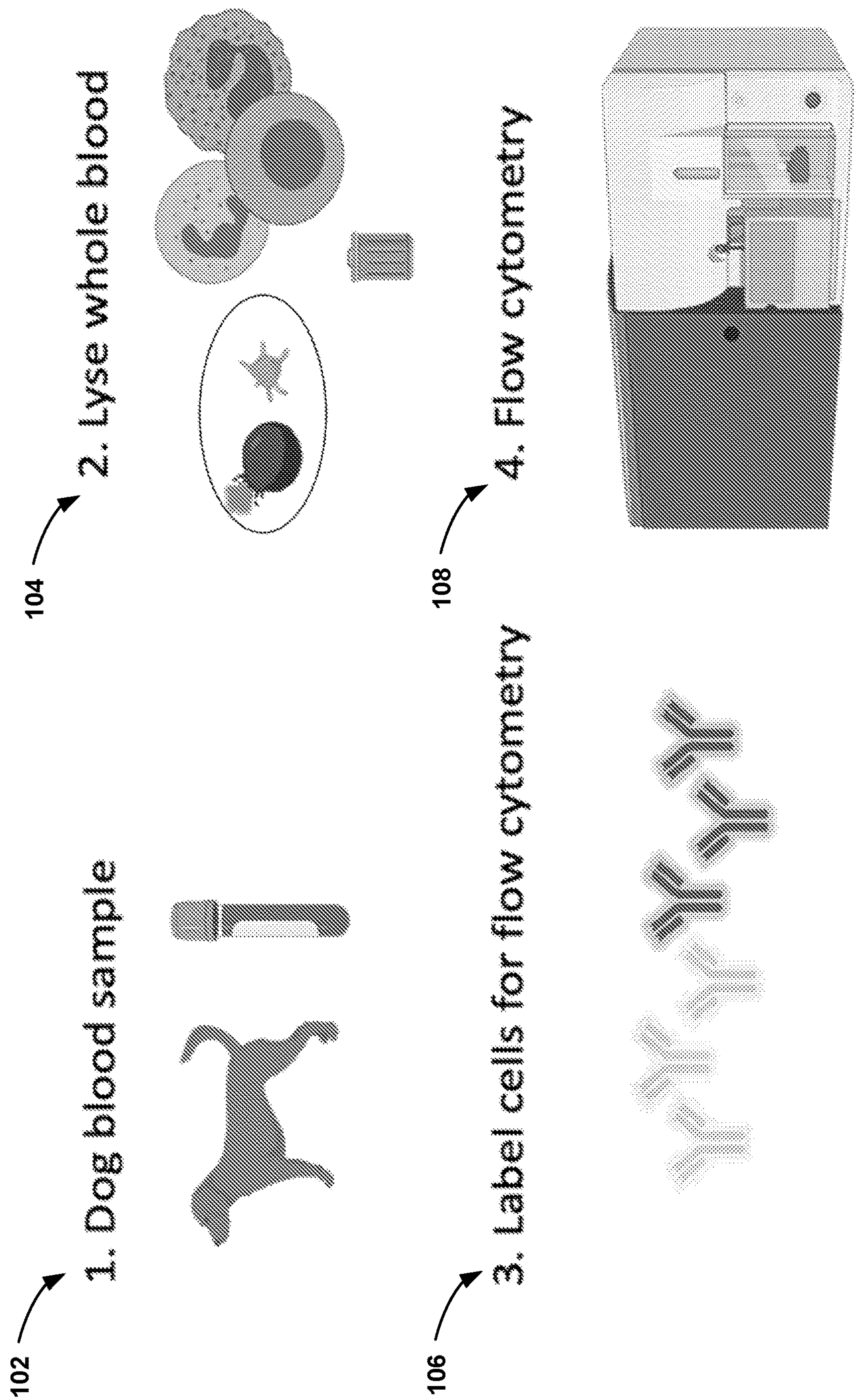
FIG. 1A is a schematic diagram illustrating an example flow cytometric detection of circulating HSA associated cells

Hemangiosarcoma (HSA) is a common malignancy in dogs that is difficult to diagnose until late onset, often resulting in death unless identified in time for emergency surgery. Once the disease is found, there is no cure for it and it is rapidly fatal. No known test is available for circulating tumor cells (CTCs), or circulating tumor-associated cells (CTACs) in a subject. Some tests are available for CTCs in epithelial tumors (carcinomas), as these are the only tumor types that express the positive marker EpCam. There are no known CTC or CTAC tests to detect sarcomas or other types of cancer, and none have been designed or approved for early detection. In some examples, a test may attempt to detect mutations by sequencing cell free tumor DNA and identifying mutations or specific molecular markers in tumor exosomes and other serum markers. In the veterinary space, an ELISA test may detect C-reactive protein and Thymidine Kinase in serum for early detection of cancer, but it would have low sensitivity and low specificity. This test cannot predict cancer type or location. A test to detect cell free tumor DNA (e.g., a BRAF mutation) in urine can identify bladder cancer in its early stages (e.g., a CADET test). However, none of these tests can provide appropriate identification of CTCs or CTACs in a subject, such as in dogs with HSA.

As described herein, systems, devices, and techniques enable the detection of CTCs or CTACs in a subject to predict the likelihood that the subject has one or more types of cancer, such as HSA. Initially, HSA associated cells can be obtained from a blood sample, labeled with one or more specific antibodies, and analyzed using flow cytometry to identify data features of the analyzed cells. HSA associated cells may include cells that are part of, or associated with the development of, a tumor, such as activated endothelial cells, hematopoietic progenitors, HSA cells, or tumor niche cells that may be in the circulation of a subject. For example, one improvement of this type of test may be its ability to identify lineage-negative cells (nonwhite blood cells) co-expressing $\alpha_v\beta_3$-integrin and CD44 in the blood. Concurrent expression of both of these markers is associated with pathology that indicates tumor-initiating or tumor propagating cells and/or alterations in the niche (e.g., the environment). Testing a blood sample in this manner may improve the outcome for the disease by enabling earlier detection of cancer cells, such as HSA cells, in blood using flow cytometry. In addition to early detection using CTC or CTAC detection, these techniques may facilitate monitoring for disease relapse. In some examples, these detection techniques for certain types of cancer, such as HSA, can be paired with a bispecific ligand targeted toxin (eBAT) therapeutic that eliminates the cells responsible for maintaining the disease. In this manner, early detection of HSA cells, for example, in circulation that are associated with the presence of incipient HSA, before tumors become established, can potentially be used to identify subjects and enable the determination of rational treatment strategies such as a bispecific ligand targeted toxin (eBAT) that can eliminate nascent tumors before the disease has become established for that subject.

In one example, a system may implement machine learning techniques to integrate information obtained from a blood test where cells are enumerated and phenotyped using flow cytometry to determine the health status and risk of a dog according to several classifications, such as four predetermined groups. The first group may include dogs with no detectable disease (e.g., a healthy group); and therefore low risk to develop one of the diseases listed in the other three groups. The second group may include dogs with non-malignant vascular pathology of the spleen (nodular hyperplasia, splenic hematomas, extramedullary hematopoiesis, etc.), or at risk to develop one of these conditions. The third group may include HSA, or at risk to develop HSA. The fourth group may include a tumor different from HSA, or at risk to develop a tumor different from HSA.

Figure 4B:
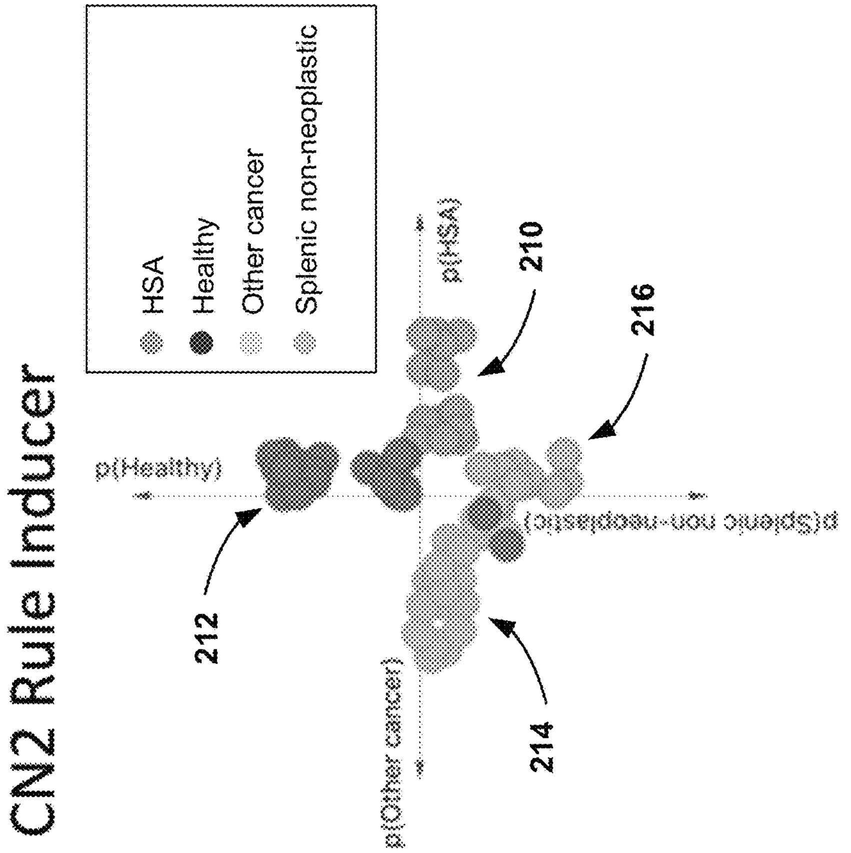
FIGS. 4A and 4B are tree plots of example training for machine learning approaches for detection of HSA.
Figure 4A:
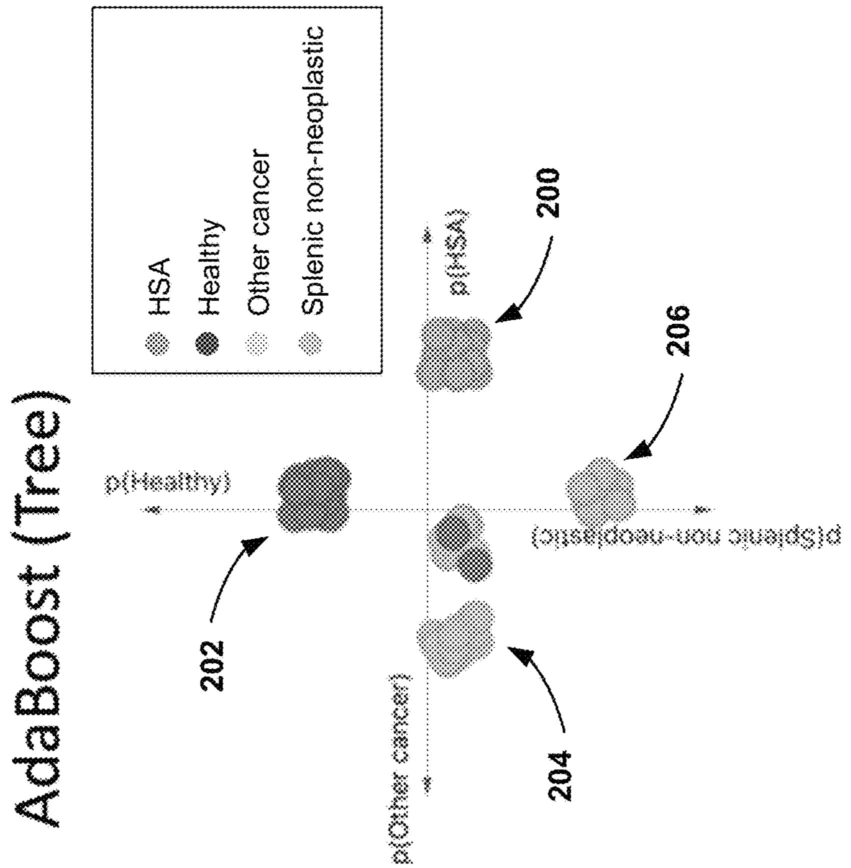

The markers used to assign or classify the blood sample from each subject to the groups include, among others, alpha-v/beta-3 ($\alpha_v\beta_3$) integrin or CD51/CD61 and markers of hematopoietic progenitors CD34 and CD177 or c-Kit, as well as lineage markers to exclude normal leukocytes. Parameters, or data features, of forward scatter (approx. cell size or volume) and side scatter (granularity/complexity) from flow cytometry measurements are also included, so cells that express $\alpha_v\beta_3$-integrin are divided into "complex, granular suspect cells" and "small, non-granular and non-complex cells." A system can then use the parameters, normalized to the number of cells analyzed (#per 100,000 cells analyzed), from samples with a known diagnosis to train and validate a plurality of machine learning algorithms (e.g., analytical models). The system can then apply the plurality of machine learning algorithms to flow cytometric measurements from unknown samples from healthy subjects, such as dogs, to classify the unknown samples into a defined "risk group" using these algorithms, as illustrated in FIGS. 4A and 4B and Table 1.

A system can characterize subjects, such as dogs, humans, or other animals, for example, into risk categories using such a blood test. The analytical models may employ a combination of parameters (e.g., data features) to distinguish between the different groups of classification options in order to characterize, or classify, the subjects into the appropriate risk categories. These risk categories may include one or more types of cancer, such as HSA.

These techniques may be used to screen dogs that are at risk for cancer development. In some examples, this would include dogs of certain breeds (e.g., golden retrievers, German Shepherd Dogs, Portuguese Water Dogs, boxers, etc.) starting at an early age, or all dogs that reach adulthood and have increasing probability of a cancer death (estimated at 50% in dogs older than 10 years). Such a test could be run annually or semiannually, and may be one of the factors used to determine if a dog would benefit from a preventative strategy, such as a ligand targeted toxin to target the malignant cells and the developing tumor niche. Although these cancer detection techniques are described herein with respect to dogs, these techniques may also be applied to other organisms such as humans.

FIG. 1A is a schematic diagram illustrating an example flow cytometric detection of circulating HSA associated cells. The process of FIG. 1A is described as being performed by a technician, but may be performed by any user, automated system, or combination thereof. In step 102, a technician obtains blood samples from subjects, such as dogs, in one of four categories (confirmed HSA, confirmed other tumor, confirmed benign vascular pathology of the spleen, and apparently healthy between 2 and 4 years old). In step 104, a technician subjects blood samples to hypotonic lysis to eliminate erythrocytes (red blood cells (RBCs)) and deplete platelets. In step 104, the technician may mark remaining leukocytes in the sample with antibodies to establish a single color "dump gate" to exclude T cells (CD5), B cells (CD22), and myeloid cells/granulocytes (CD11b+/−CD45). The technician may mark circulating HSA-associated cells with specific antibodies that recognize markers such as $\alpha_v\beta_3$-integrin and hematopoietic progenitor markers CD34 and CD117 and/or $\alpha_v\beta_3$-integrin and the hyaluronic acid receptor CD44. The technician may then place the samples within a flow cytometer so that the multi-parameter flow cytometer can analyze the samples. In some examples, additional steps may be provided at any point within the process of FIG. 1A.

Figure 1B:
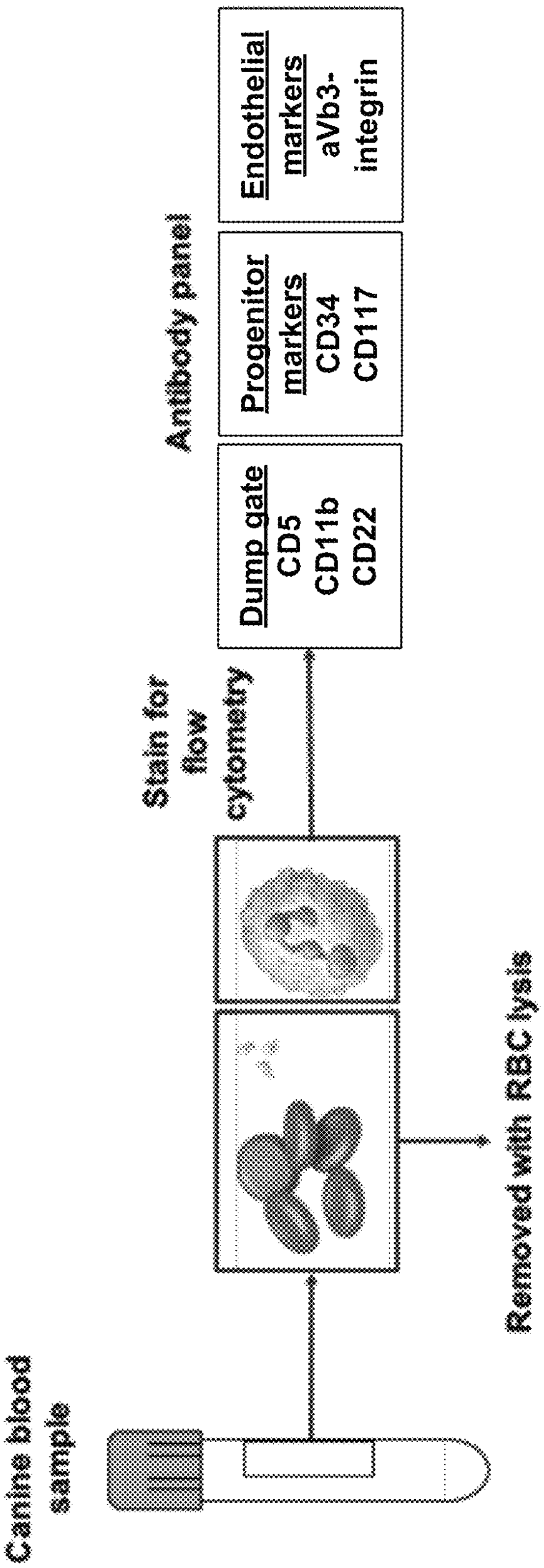
FIG. 1B is a schematic diagram illustrating an example flow cytometric detection of circulating HSA associated cells.

FIG. 1B is a schematic diagram illustrating an example flow cytometric detection of circulating HSA-associated cells. FIG. 1B may be similar to the process of FIG. 1A. As shown in FIG. 1B, blood samples are initially taken from a subject and then subjected to RBC lysis, and remaining leukocytes are marked with antibodies to establish a "dump gate." These dump gate antibodies may include CD5, CD11b, and/or CD22. Circulating HSA-associated cells may also be marked with specific antibodies that recognize $\alpha_v\beta_3$-integrin (e.g., endothelial markers) and hematopoietic progenitor markers CD34 and CD117.

In some examples, flow cytometry is used to generate data features for blood sample detection of CTCs or CTACs from canine blood samples. The tests use an antibody panel to exclude normal leukocytes and to identify CTCs or CTACs, with a combination of progenitor markers, CD34 and c-kit, and an activated endothelial marker, integrin alpha(v)beta(3) ($\alpha_v\beta_3$). A lower limit of detection for CTCs was established by spiking cultured HSA cells into normal blood. CTACs were enumerated in blood samples from dogs with HSA (n=13), splenic hematoma (n=12), cancer other than HSA (n=23), and no known disease (n=25). Some parameters may exclude monocytes, platelets, or all leukocytes, as well as to detect co-expression of the hyaluronic acid receptor (CD44).

Figure 22C:
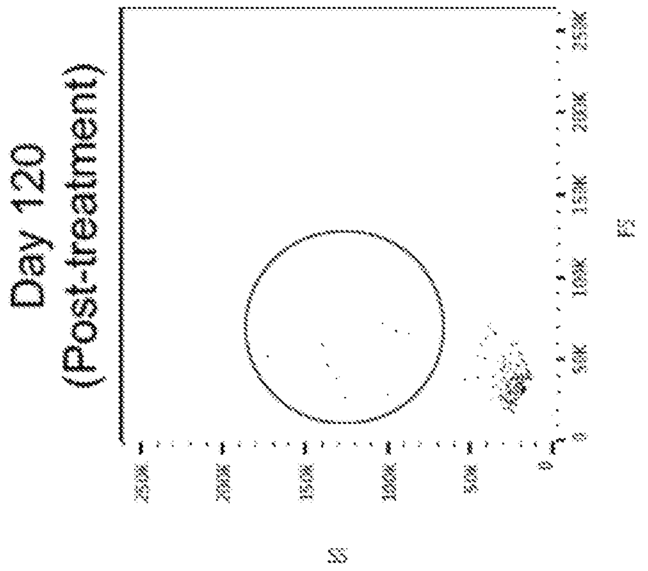
FIGS. 22A, 22B, and 22C are cytograms of the side and forward angle light scatter (SS and FS) from cells pre- and post-treatment.
Figure 22B:
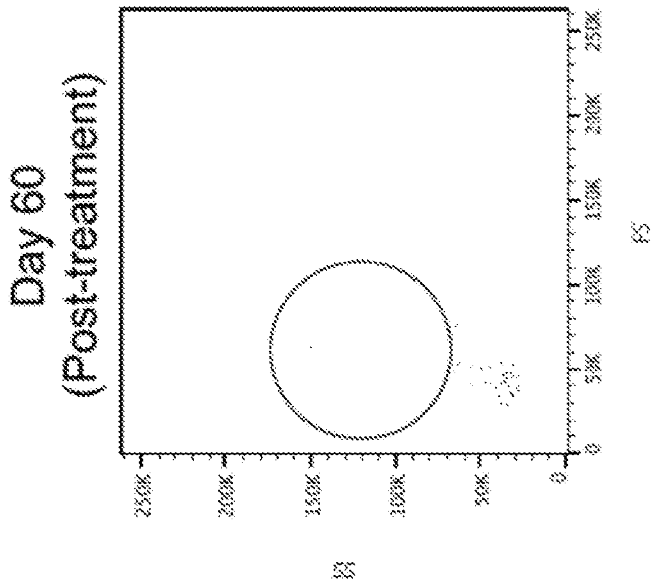
Figure 22A:
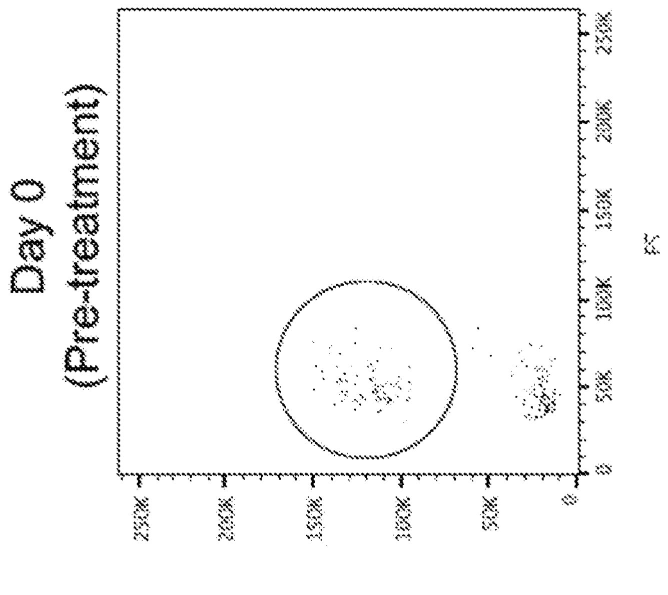

Using the techniques described herein, the system can detect as few as 1 to 5 HSA cells per 100,000 nucleated cells in blood of apparently healthy dogs. Canine platelets expressed $\alpha_v\beta_3$-integrin and CD44, but not CD45; and canine HSA cells expressed CD41/CD61. Cells co-expressing $\alpha_v\beta_3$-integrin with CD34 and/or c-kit were only detected in a small number of blood samples, as these cells may represent CTCs. However, $\alpha v\beta_3$-integrin+ cells were more prevalent in dogs with HSA than in healthy dogs and in dogs with cancer other than HSA. These $\alpha v\beta_3$-integrin+ cells are being back gated to see where they lay on the SS v. FS plot, such as the plot shown in FIG. 2A. In some examples, the SS-low population is prevalent in samples from dogs that do not have HSA, whereas the SS-high is present in samples from dogs with HSA, and in some samples from dogs with splenic hematoma, but not samples from healthy dogs. The addition of CD45 causes the majority of the low cells on the plot to be gated out. In subsequent samples from patient samples with detectable CTCs or CTACs, we see decrease, or complete elimination of these cells after treatment, as shown in FIGS. 22A, 22B, and 22C.

These tests show that $\alpha v\beta_3$-integrin+ cells are detectable in blood of dogs with HSA using flow cytometry. Although these $\alpha v\beta_3$-integrin+ cells may be CTCs and/or CTACs, these $\alpha v\beta_3$-integrin+ cells may also include activated endothelial cells or platelet-coated leukocytes. The addition of CD45 to this panel improved the specificity of this test, by gating out cells, such as monocytes, that would otherwise not be excluded.

Figure 2C:
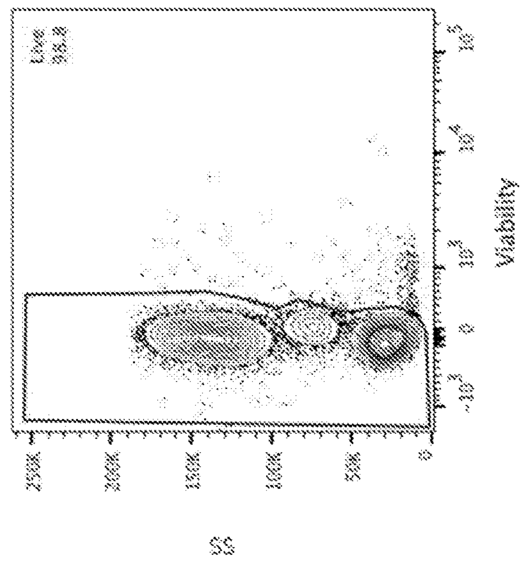
FIGS. 2A, 2B, 2C, 2D, and 2E are graphs illustrating an example gating strategy.
Figure 2B:
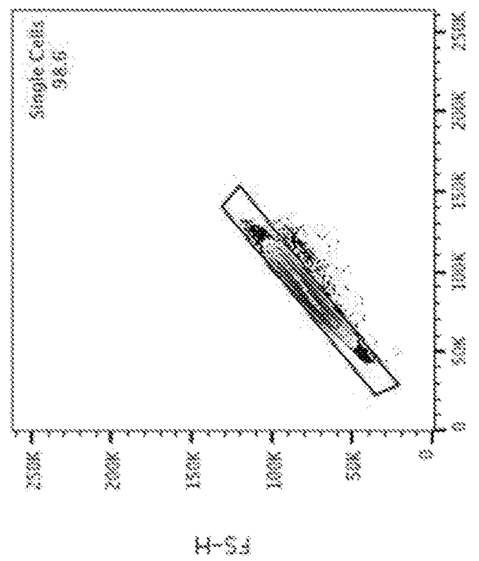
Figure 2A:
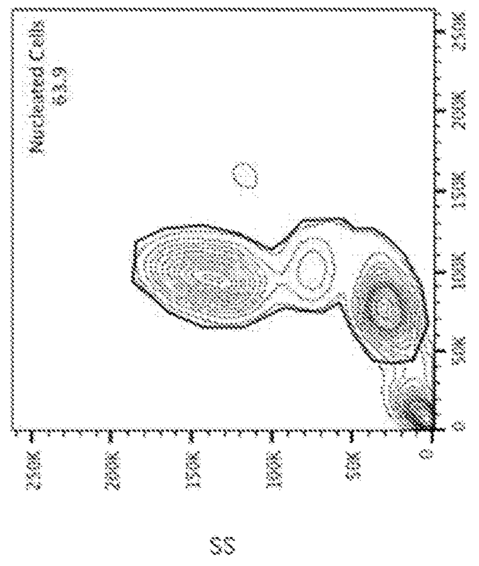
Figure 2D:
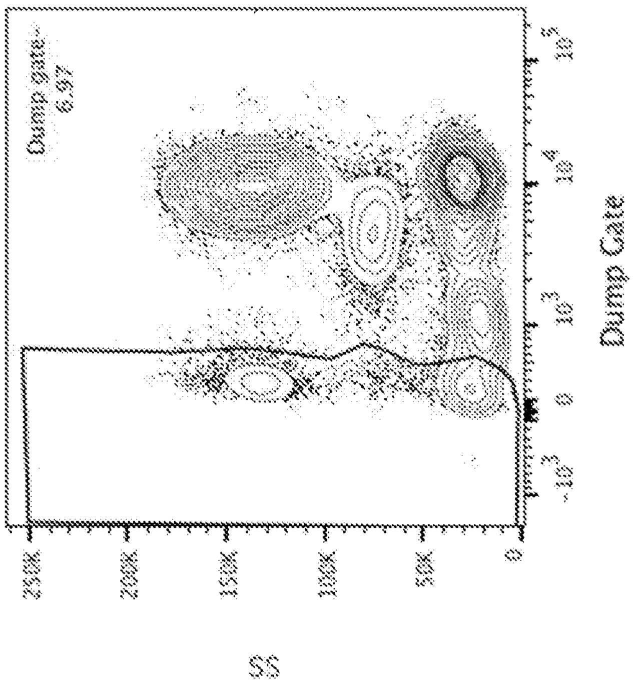
Figure 2E:
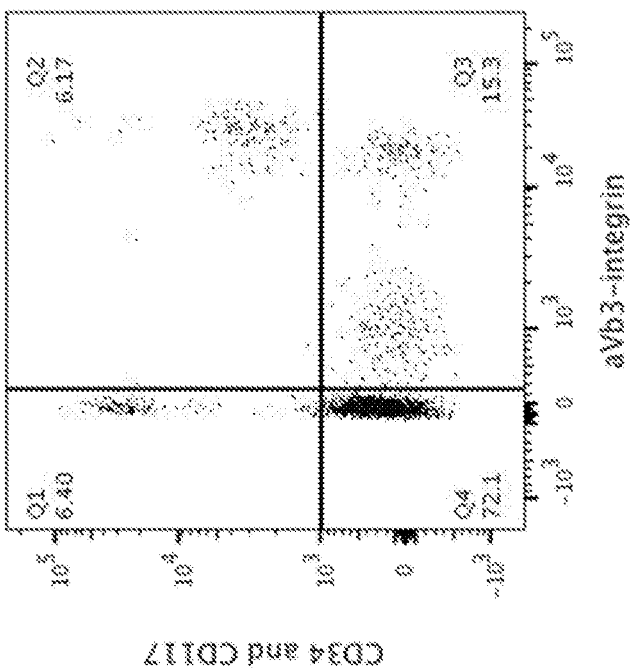

FIGS. 2A, 2B, 2C, 2D, and 2E are graphs illustrating an example gating strategy. Each of the FIGS. 2A-2E shows a progression of excluding unwanted cells from analysis. The initial gate of FIG. 2A includes leukocyte populations and excludes debris using light scatter properties (forward and side scatter). FIG. 2B illustrates the exclusion of doublets by gating on the diagonal of FS-height vs. FS amplitude. The same outcome can be achieved using SS-height vs. SS amplitude. FIG. 2C illustrates the exclusion of dead cells using a viability stain. As shown in FIG. 2D, leukocytes are excluded using the "dump gate," in this case, with the dump gate markers labeled in the same color. A multiplexed live gate can be used with each antibody or marker in the dump gate labeled in different colors. Live cells that are not captured in the dump gate (as shown in FIG. 2D) are analyzed by plotting events into quadrants according to expression of CD34/CD117 as a function of $\alpha_v\beta_3$-integrin, as shown in FIG. 2E. Cells are visualized in 2-dimensional plots. Separation into quadrants is used for visualization, and to aid in sorting cells for further analysis as described further below with respect to FIGS. 7A-14D, for example.

Figure 3C:
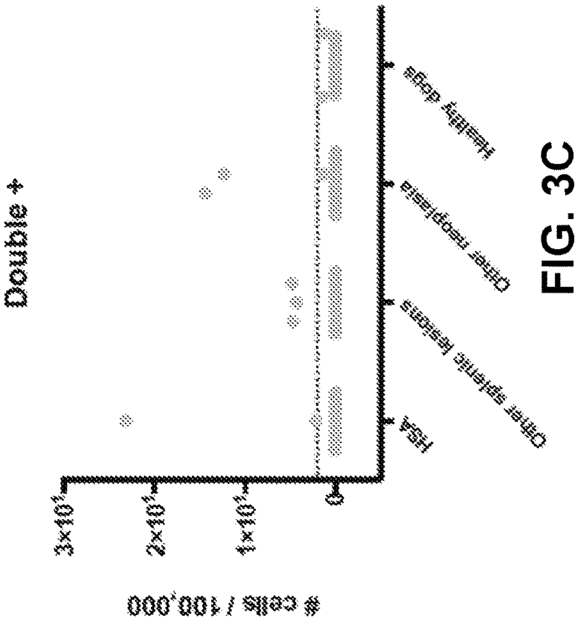
FIGS. 3A, 3B, and 3C are graphs illustrating the number of detected cells for dogs with different conditions.
Figure 3B:
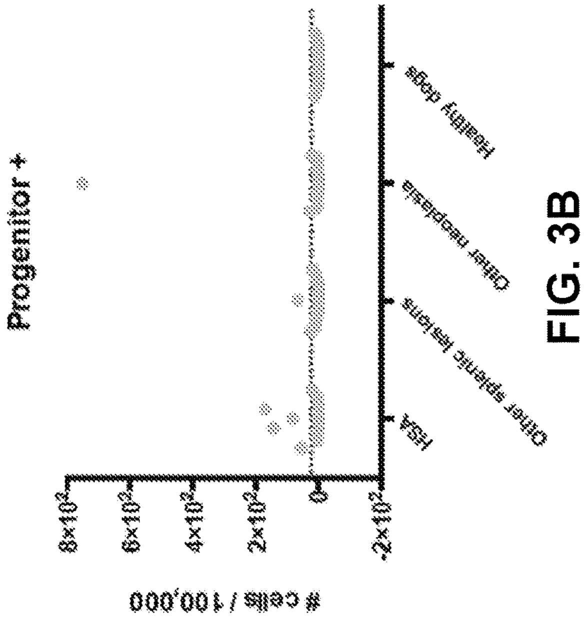
Figure 3A:
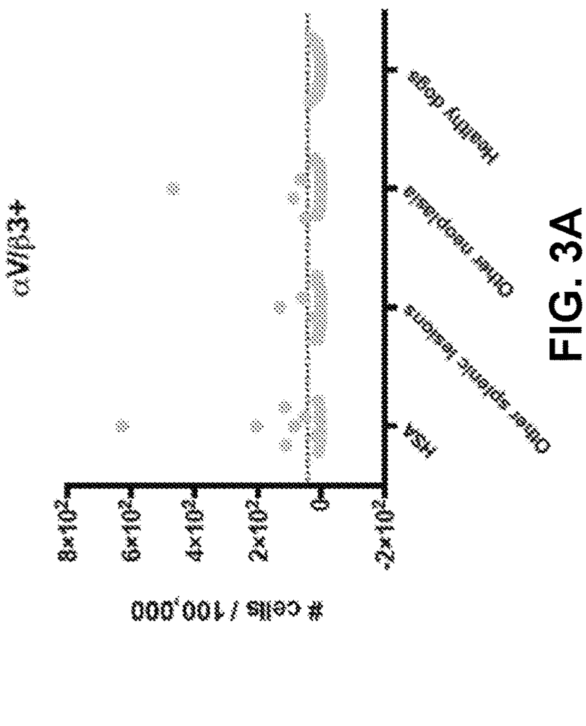

FIGS. 3A, 3B, and 3C are graphs illustrating the number of detected cells for dogs with different conditions, according to the univariate threshold analysis for example phase 1 data (data used to support analysis of FIGS. 3A-4F). Phase 1 may include analysis of circulating $\alpha v\beta_3$-integrin and CD34/CD117 single positive and double positive events in circulation from healthy dogs between 2 and 4 years old, and from dogs with HSA, other benign splenic lesions, or non-HSA cancers. Data were normalized to 100,000 nucleated events analyzed. For each marker, a threshold for positivity was set at the maximum value (+2 standard deviations) for healthy dogs. Using these parameters, there is high certainty for true positives (specificity to detecting an abnormality), but there is a high level of uncertainty for negative values (low sensitivity for absence of disease). In this manner, one or two biomarkers alone to determine the number of cells present in a sample may not be sufficient to establish a diagnosis for the subject. Instead, as shown in FIGS. 4A and 4B, machine learning algorithms may employ multiple data factors to more accurately classify samples from a subject.

FIGS. 4A and 4B are tree plots of example training for machine learning approaches for detection of HSA. As shown in FIGS. 4A and 4B, respective example analytical models (e.g., machine learning algorithms), can be trained to classify blood samples from different subjects into different classification options (e.g., different groups such as HSA, healthy, another non-HSA cancer, or a splenic non-neoplastic hematoma). FIG. 4A shows the classification of the samples according to the AdaBoost analytical model. Group 200 is classified as HSA, group 202 is classified as Healthy, group 204 is classified as another non-HSA cancer, and group 206 is a splenic non-neoplastic hematoma. There is a small group of samples clustered near the middle where the probabilities are about equal for several classifications. FIG. 4B shows the classification of the sample samples according to the CN2 Rule inducer analytical model. Group 210 is classified as HSA, group 212 is classified as Healthy, group 214 is classified as another non-HSA cancer, and group 216 is a splenic non-neoplastic hematoma. These tree- and rule-based algorithms (AdaBoost and CN2, respectively) show trainability of data using the top two data features for the blood samples. All samples were used in training, and predictions were made against the trained data set. Plots show relative prediction probability, where both methods have >0.70 accuracy across all categories, or classification options.

The results of each of the classifications shown in FIGS. 4A and 4B are also shown in Tables 1 and 2 below. Table 1 provides a confusion matrix for the AdaBoost analytical model, and Table 2 shows the confusion matrix for the CN2 rule analytical model. Each of these analytical models show prediction (proportion of actual) for 32 samples obtained from clinically healthy dogs considered to be "at risk" (based on age and breed) from phase 3 of a study. The data suggest that as many as 50% of cases might have circulating cells associated with an inapparent disease state (HSA, benign splenic lesions, or non-HSA cancer).

TABLE 1

Confusion matric for AdaBoost (showing proportion of actual)

| | | Predicted | | | | |
|---|---|---|---|---|---|---|
| | | HSA | Healthy | Other Cancer | Splenic non-neoplastic | Σ |
| Actual | HSA | NA | NA | NA | NA | |
| | Healthy | 7.8% | 54.7% | 15.6% | 21.9% | 64 |
| | Other cancer | NA | NA | NA | NA | |
| | Splenic non-neoplastic | NA | NA | NA | NA | |
| | Σ | 5 | 35 | 10 | 14 | 64 |

TABLE 2

Confusion matric for CN2 rule indicator (showing proportion of actual).

| | | Predicted | | | | |
|---|---|---|---|---|---|---|
| | | HSA | Healthy | Other Cancer | Splenic non-neoplastic | Σ |
| Actual | HSA | NA | NA | NA | NA | |
| | Healthy | 12.5% | 50.0% | 6.2% | 2% | 64 |
| | Other cancer | NA | NA | NA | NA | |
| | Splenic non-neoplastic | NA | NA | NA | NA | |
| | Σ | 8 | 32 | 4 | 20 | 64 |

From the above data shown in Tables 1 and 2, data features obtained from flow cytometry of blood samples from different subjects were trainable using machine learning tools. These trained analytical models may be able to predict which subjects may have early stages of a disease such as HSA. For example, as many as 50% of these otherwise healthy dogs may have inapparent disease. For those dogs predicted to be at risk of developing HSA, for example, it may be appropriate to develop treatment strategies such as justifying the use of cancer chemoprevention using eBAT or other appropriate approaches.

Figure 4D:
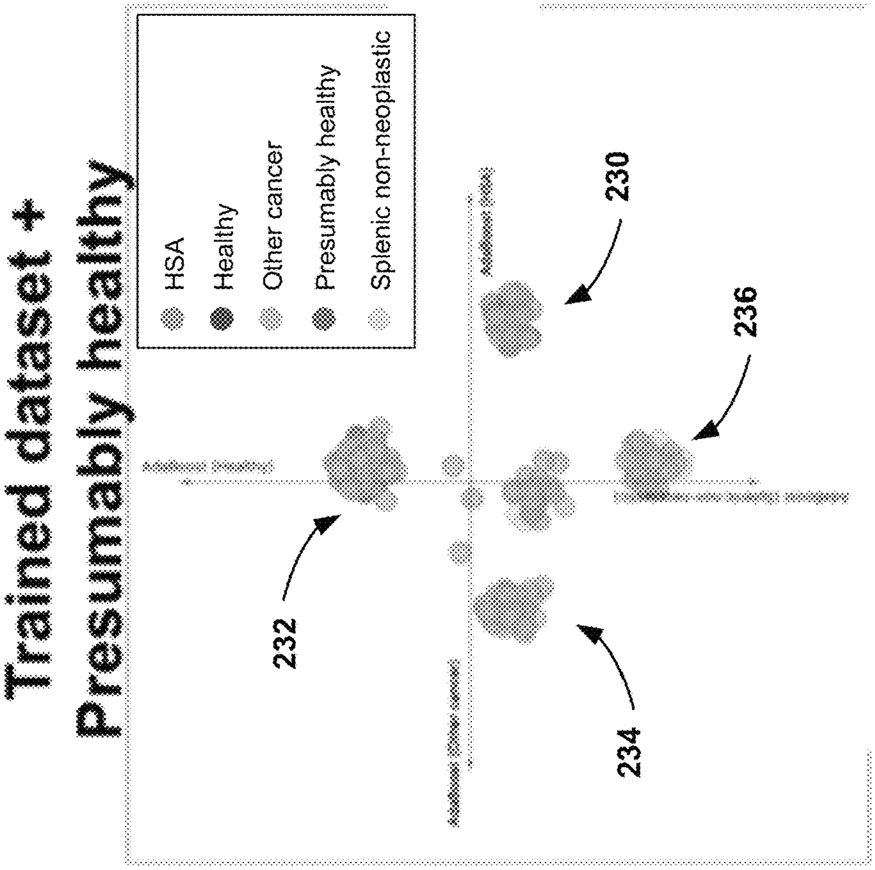
FIGS. 4C and 4D are tree plots of example training and application of machine learning approaches for detection of HSA.
Figure 4C:
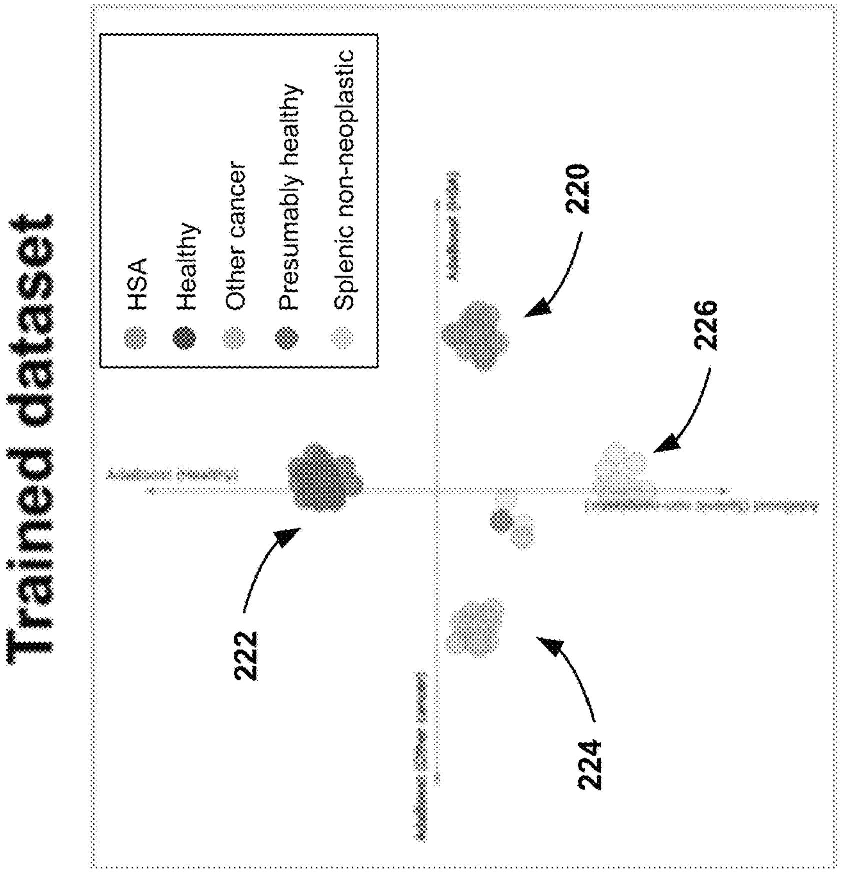
Figure 4E:
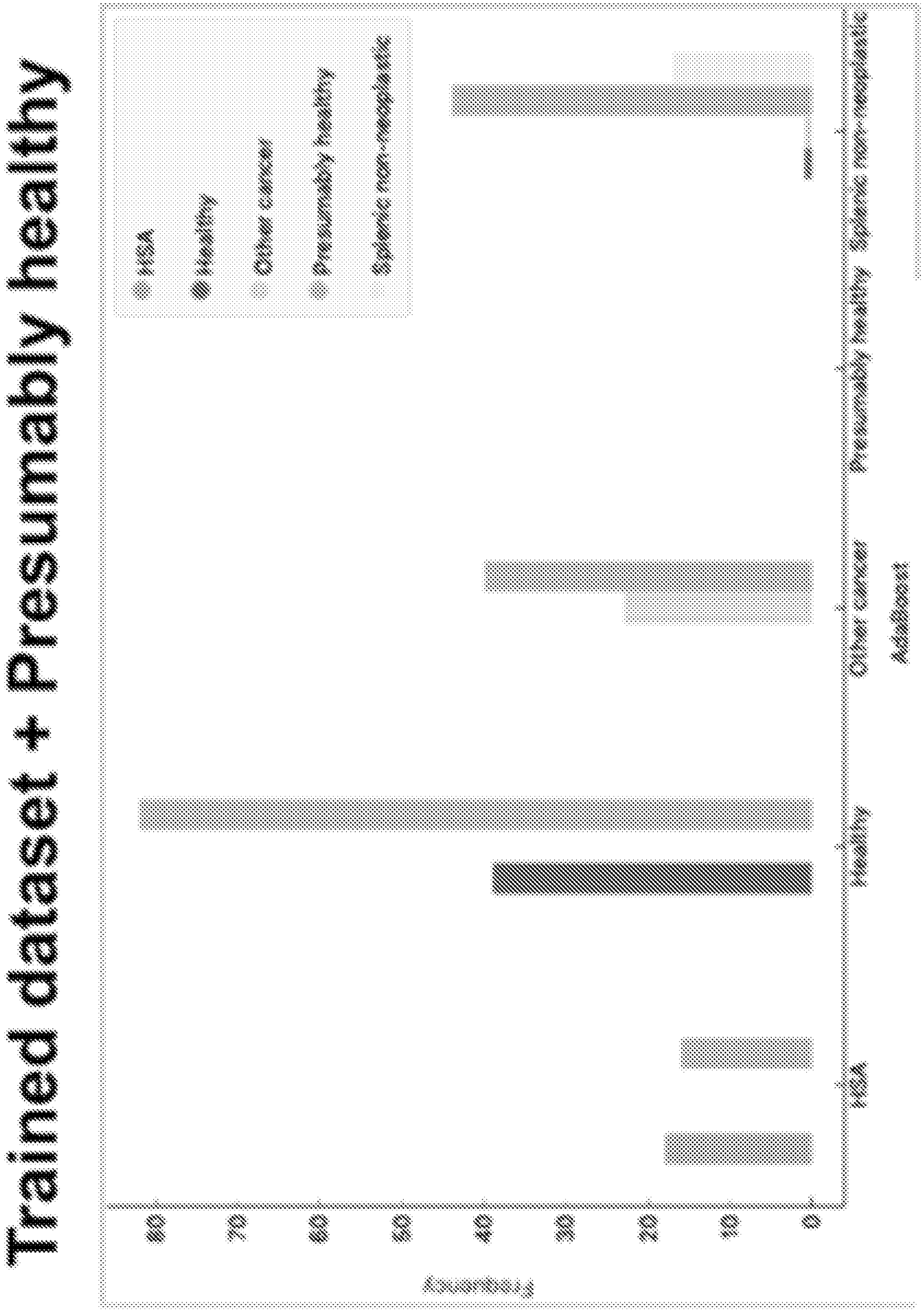

FIGS. 4C and 4D are tree plots of example training and application of machine learning approaches for detection of HSA. As shown in FIG. 4C, duplicate samples from 99 dogs with a definitive classification (n=198) were used to train the machine learning algorithms (e.g., analytical models) applying 10-fold cross validation/leave-one-out analysis methods. Group 220 is classified as HSA, group 222 is classified as Healthy, group 224 is classified as another non-HSA cancer, and group 226 is a splenic non-neoplastic hematoma. The classification accuracy for the top-8 independent machine learning algorithms was about 80% (80.4%+/−2.6). Duplicate samples from 91 presumably healthy boxers, golden retrievers, or Portuguese Water Dogs between the ages of 6 and 15 (n=182) were then used for prediction, as shown in the tree plot of FIG. 4D. Group 230 is classified as HSA, group 232 is classified as Healthy, group 234 is classified as another non-HSA cancer, and group 236 is a splenic non-neoplastic hematoma. None of the samples from the presumably healthy dogs were used for training, in this case. FIG. 4E illustrates the frequency of samples in each classification (known and presumably healthy). The presumably healthy samples are those samples that are being screened, or tested, using the trained analytical models. FIG. 4F illustrates the distribution of samples as a percent for each group. Note particularly that no healthy dogs are classified as having HSA, but almost 9% of presumably healthy dogs between the ages of 6 and 15 are classified as being at risk for HSA, 22% are classified as being at risk for other cancers, and 24% are classified as being at risk for non-malignant vascular pathology. These percentages may be similar to typical cancer rates with dog populations in this age group.

As discussed above flow cytometry may be used to obtain measurements and parameters, of data features, that may help to detect subject at risk for certain diseases, such as a cancer (e.g., HSA). Markers of activated endothelial cells ($\alpha v \beta_3$-integrin or CD51/CD61) combined with markers of hematopoietic progenitors (CD34 and CD177 or c-Kit) may be used to detect HSA cells, and specifically presumed "HSA stem cells," or "HSA-associated cells," such as tumor niche cells, in the circulation of a subject. The technique for detection of "HSA stem cells" is described in detail in U.S. Pat. No. 7,910,315 issued to Modiano et al. and entitled "Early Detection of Hemangiosarcoma and Angiosarcoma," the entire contents of which are incorporated herein by reference. In addition to these markers, as discussed herein, HSA detection may be improved by adding the panleukocyte marker CD45 and the hyaluronic acid receptor, CD44, to the detection panel for flow cytometry, as well as by recognition that some of the events are "HSA-associated cells" or CTACs whose features are incorporated into the training of algorithms for disease classification.

Blood samples obtained from dogs are processed by lysing and staining for flow cytometry. In addition to the markers analyzed for cells that do not express lineage markers (CD5, CD22, CD11b, combined to create a "dump gate"), the markers CD45 and CD44 are added individually and in combination (in one of the staining variables, CD45 is included in the dump gate) to improve on the detection of cells associated with malignancies. The origin of the cells as cancer stem cells (CTCs) or niche cells (CTACs) may not be needed to interpret the results of the assay. Instead, the number and phenotype of these cells and their association with specific conditions are used in this detection process. In this manner, the CD44 and CD45 marker addition may aid in the early detection of cancer, such as HSA, in dogs in its earliest stages when cancer cells are creating a growth niche and before the tumor is formed. Early detection makes rational intervention strategies to prevent cancer in animals at high risk possible.

Figure 5B:
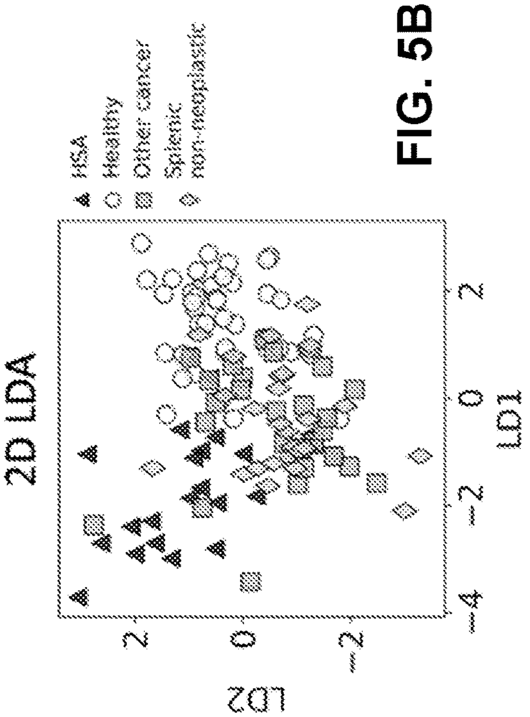
FIGS. 5A, 5B, and 5C are graphs of example principal component analysis (PCA) and linear discriminant analysis (LDA) plots for classification of analyzed samples.
Figure 5C:
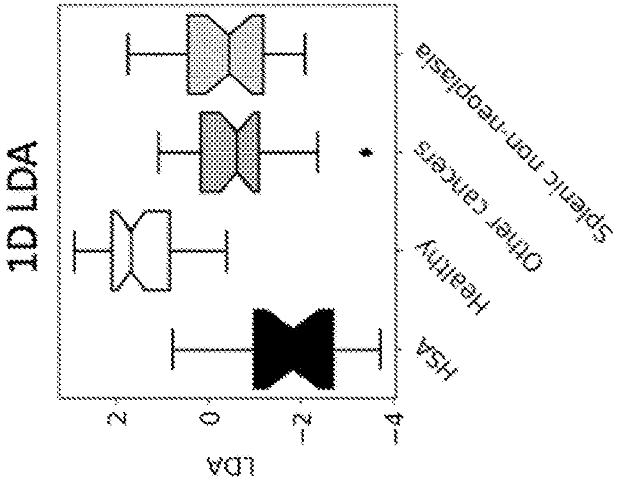
Figure 5A:
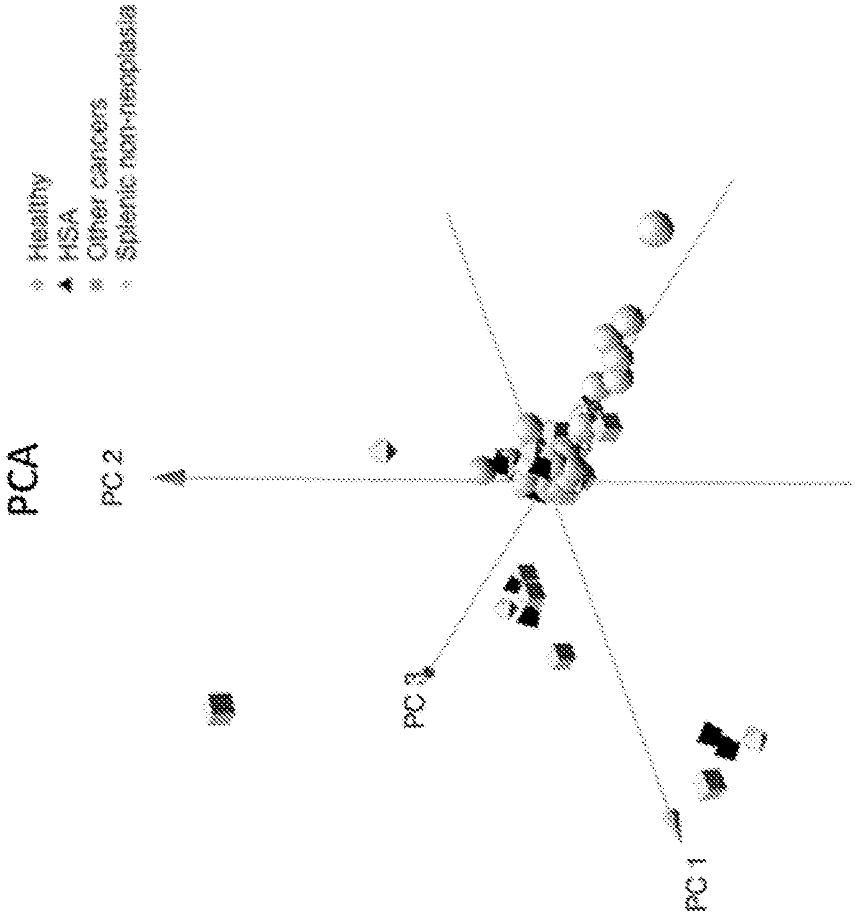

FIGS. 5A, 5B, and 5C are graphs of example principal component analysis (PCA) and linear discriminant analysis (LDA) plots for classification of analyzed samples. The data used in the analysis discussed with respect to FIGS. 5A-16 may include additional samples than Phase 1 discussed above. The techniques and processes described with respect to FIGS. 5A-16 may be similar to the processes discussed with respect to FIGS. 2A-4F in some examples. However, there may be differences as well in the analysis of sample data in order to identify a likelihood or probability that a subject has HSA or is likely to develop HSA.

As shown in FIG. 5A, the graph is a 3-dimensional PCA plot showing clustering of 117 samples from four categories (21 sample of HSA, 41 samples of healthy, 29 samples of other cancers, and 26 samples of splenic non-neoplasia) described in FIG. 1A and stained with CD34/CD117 and $\alpha_v\beta_3$-integrin as described in FIGS. 2A-2E. The analysis includes 33 features extracted from flow data (e.g., from flow cytometry), achieving some degree of separation among categories. One or more machine learning algorithms may be trained and applied to the data in order to determine the separation among categories similar to the discussion with respect to FIGS. 4A and 4B. While the separation achieved may be insufficient to assign a definitive classification to every sample, the separation may enable further analysis. As shown in FIG. 5B, the same samples from FIG. 5A are shown in a 2-dimensional linear discriminant analysis. This 2-dimensional linear discriminant analysis provides a more robust separation, especially for the HSA category, as illustrated in the 1-dimensional notched box plot of FIG. 5C showing LDA-transformed data as a function of categories.

Figure 6B:
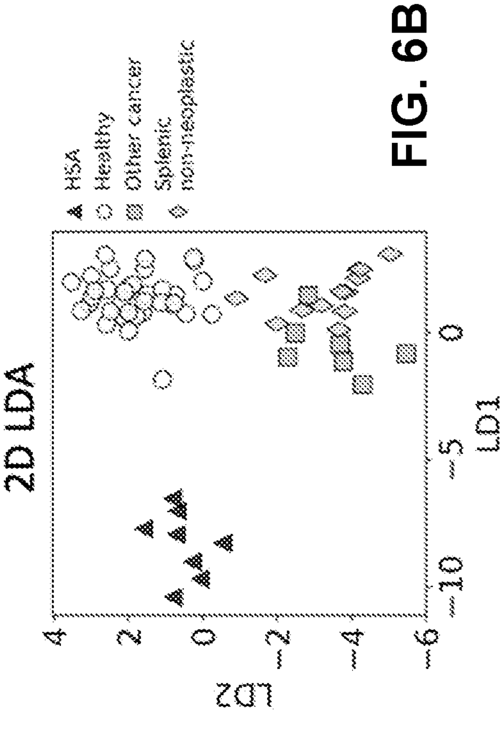
FIGS. 6A, 6B, and 6C are graphs of example principal component analysis (PCA) and linear discriminant analysis (LDA) plots for classification of analyzed samples.
Figure 6C:
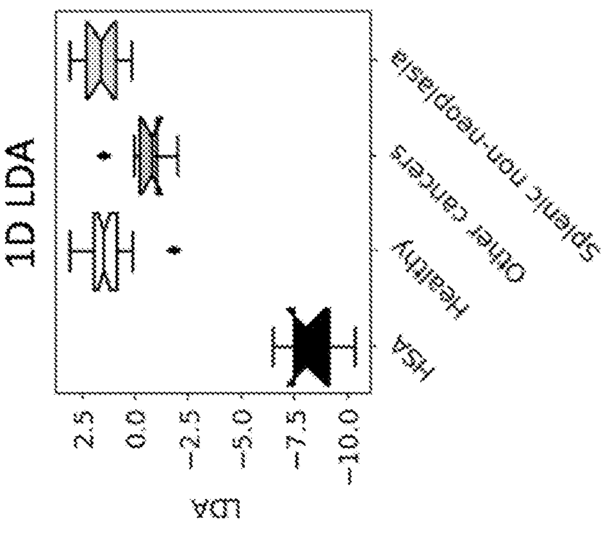
Figure 6A:
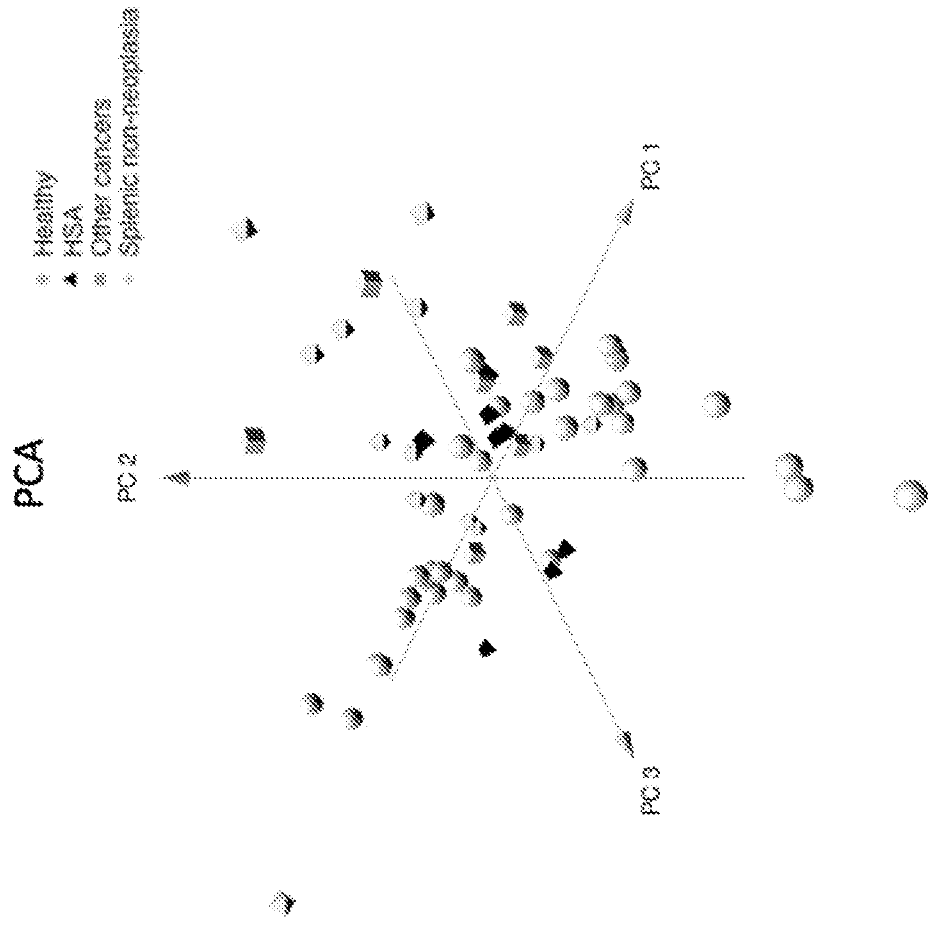

FIGS. 6A, 6B, and 6C are graphs of example principal component analysis (PCA) and linear discriminant analysis (LDA) plots for classification of analyzed samples. The 3-dimensional PCA plot of FIG. 6A shows clustering of 64 samples from four categories (8 subjects of HSA, 36 subjects of healthy, 7 subjects of other cancers, and 13 subjects of splenic non-neoplasia) described in FIG. 1A and stained with CD34/CD117, CD44, CD45, and $\alpha_v\beta_3$-integrin as described in FIGS. 2A-2E. The example analysis includes 42 features extracted from flow data achieving improved separation among categories than the 33-feature analysis, especially for the HSA samples. One or more machine learning algorithms may be trained and applied to the data in order to determine the separation among categories similar to the discussion with respect to FIGS. 4A and 4B and elsewhere herein. FIG. 6B provides a graph of the same samples from FIG. 6A shown in a 2-dimensional linear discriminant analysis. This 2-dimensional linear discriminant analysis achieves a robust separation among categories, as shown in the 1-dimensional notched box plot of FIG. 6C showing LDA-transformed data as a function of categories.

FIGS. 7A, 7B, 7C, 7D, 7E, and 7F are graphs of example machine learning algorithm performance using different features from data. Different machine learning algorithms (e.g., analytical models) were trained to build different models for optimization and training, including Logistic Regression (LR), Linear Discriminant Analysis (LDA), k-nearest neighbors (kNN), Classification and Regression Trees (CART), Gaussian Naïve Bayes (NB), Support Vector Machine (SVM), Bagging (BAG), Random Forest (RF), Extra Trees Classifier (EXT), Adaptive Boosting (AdaBoost or ADA), Stochastic Gradient Boosting (SGB), and Neural Network (NN) algorithms. In other examples, Decision Tree Classifier (Tree), Deep Learning (DL), or other algorithms may be used. Machine learning performance using 33-feature data (FIGS. 7A-7C) and 42-feature data (FIGS. 7D-7F) are provided for the detection of HSA. Box and whiskers probability plots show sensitivity (true positive rate, filled boxes) and specificity (true negative rate, clear boxes) for 12 distinct machine learning algorithms using training and 10 random iterations of 10-fold cross validation with 33 features (data from FIGS. 5A-5C) and 42 features (data from FIGS. 6A-6C).

Figures 7A, 7B, 7C, 7D, 7E, 7F:
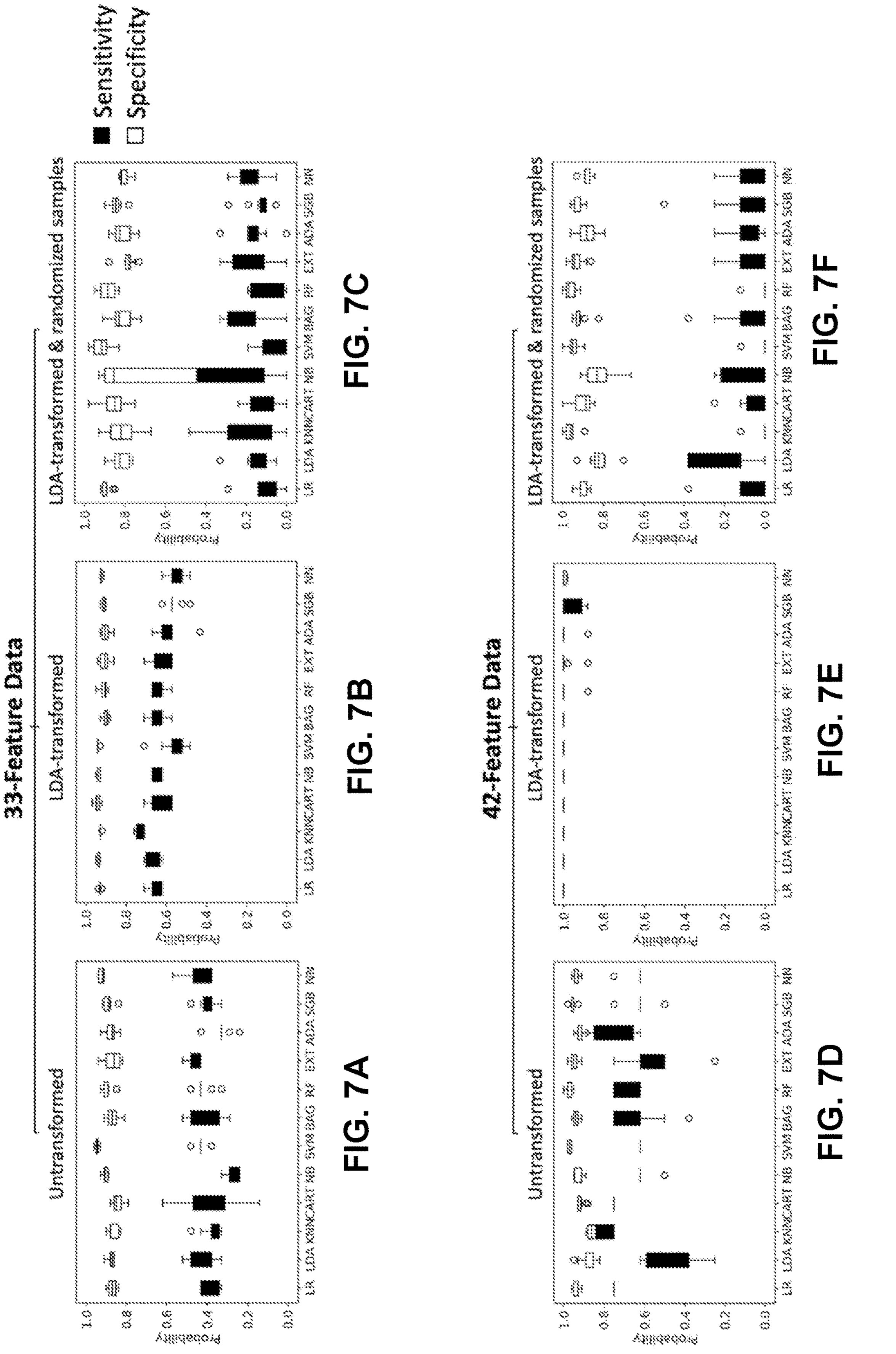
FIGS. 7A, 7B, 7C, 7D, 7E, and 7F are graphs of example machine learning performance using different features from data.

FIG. 7A illustrates performance of the assay using untransformed data from 33 features and machine learning. FIG. 7B illustrates improvement of the assay performance using LDA-transformed data from 33 features and machine learning. FIG. 7C illustrates control analysis supporting the application of the assay with 33 features to the four defined categories (e.g., the determinations for each subject). In this analysis, the number of samples assigned to each category remained constant, but the categorical assignment for each sample was randomized. Note the reduction in specificity and the marked reduction in sensitivity of the assay for every algorithm for the randomized assignments. This reduction in specificity and sensitivity indicates that the machine learning algorithms are correctly classifying the samples.

FIG. 7D illustrates performance of the assay using untransformed data from 42 features and machine learning. Note the improved performance using data from the 42 features over the analysis using untransformed data from 33 features of FIG. 7A. FIG. 7E illustrates an improvement of the assay performance using LDA-transformed data from 42 features and machine learning using the example machine learning models. Note the improved performance over the analysis using untransformed data from 42 features as well as LDA-transformed data from 33 features. FIG. 7F illustrates control analysis supporting the application of the assay with 42 features to the four defined categories (e.g., the determinations for each subject). In this analysis, the number of samples assigned to each category remained constant, but the categorical assignment for each sample was randomized. Note the reduction in specificity and the marked reduction in sensitivity of the assay for every algorithm for the randomized assignments. This reduction in specificity and sensitivity indicates that the machine learning algorithms are correctly classifying the samples. The sum of the data presented here can be used to assign a risk level for HSA to a subject dog, for example, as "high risk" when there is high concordance for HSA among the machine learning algorithms, "medium risk" when one or more, but not all algorithms predict HSA, or "low risk" when there is high concordance for a condition other than HSA. In other examples, only a high risk and low risk of HSA may be output. In some examples, in addition, or alternatively, to the high and low risk of HSA, the system may output a risk or probability of other conditions, such as a cancer other than HSA, a splenic hematoma, and/or a healthy classification.

Figure 8A:
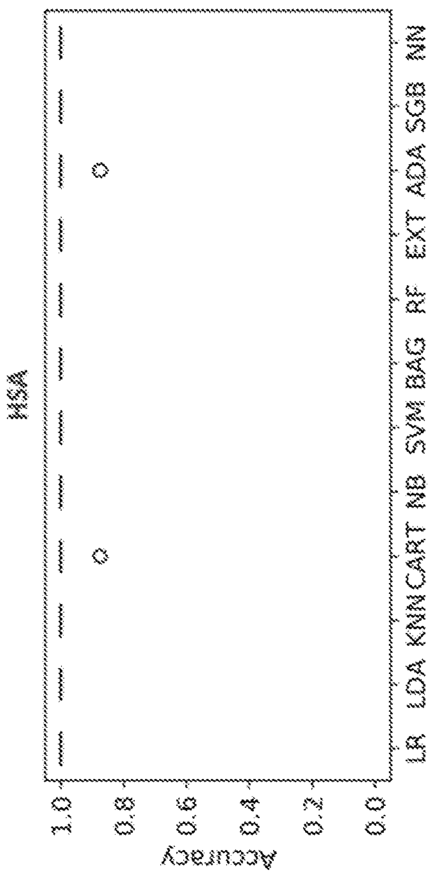
FIGS. 8A, 8B, 8C, and 8D are graphs of example machine learning accuracy for different classifications of samples.
Figure 8B:
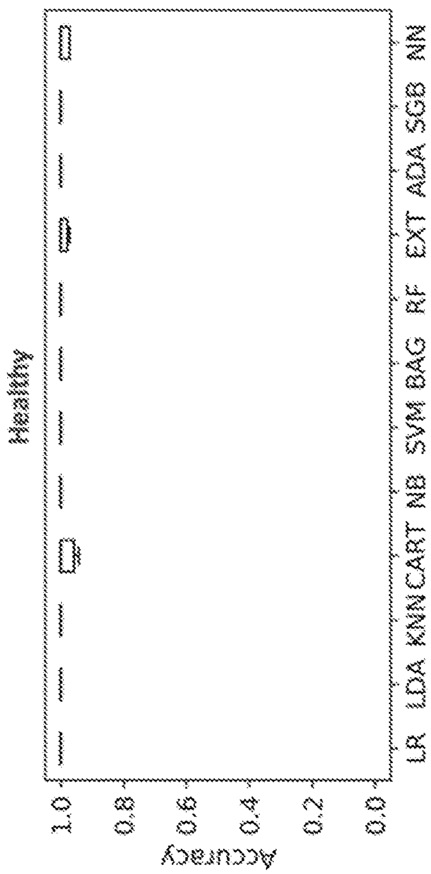
Figure 8C:
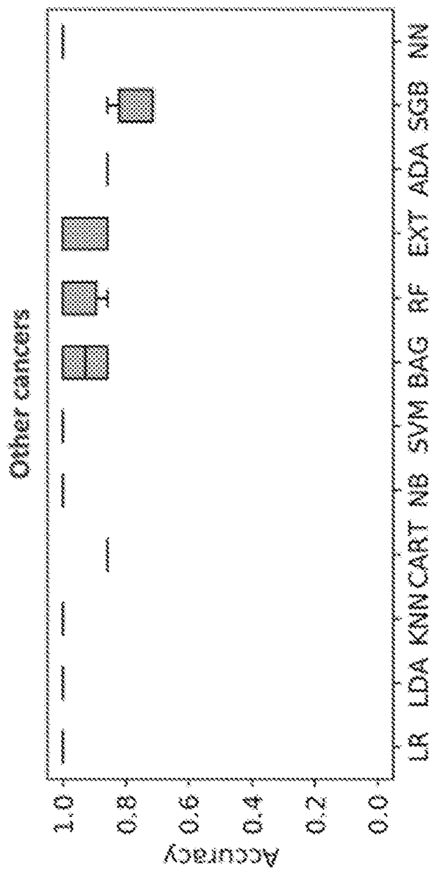
Figure 8D:
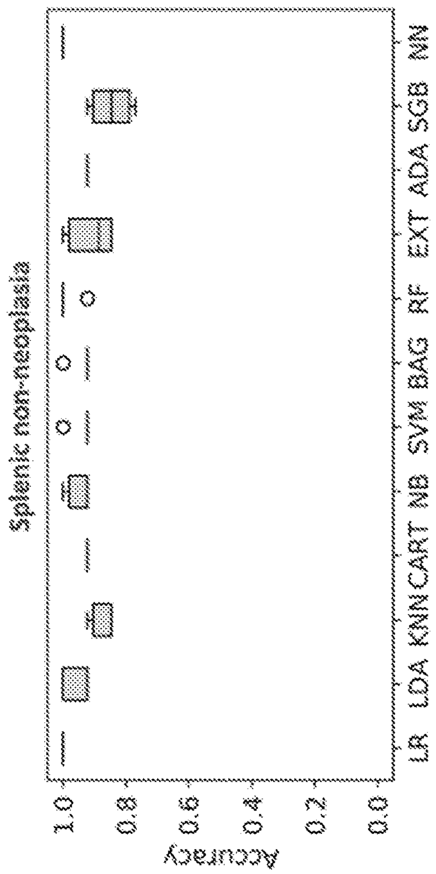

FIGS. 8A, 8B, 8C, and 8D are graphs of example machine learning accuracy for different classifications of samples. These figures provide a summary of LDA transformed 42-feature machine learning classification accuracy for assignment of canine samples into HSA, other cancers, benign vascular pathology, or presumably healthy categories. Box and whiskers probability plots showing the classification accuracy (the accuracy of prediction) for each category across 12 distinct machine learning algorithms using training and 10 random iterations of 10-fold cross-validation with 42 features (data from FIGS. 6A-6C). FIG. 8A indicates classification accuracy for HSA category, and FIG. 8B illustrates classification accuracy for presumably healthy category of subjects. FIG. 8C illustrates classification accuracy for other cancers category, and FIG. 8D illustrates classification accuracy for benign vascular pathology ("splenic non-neoplasia") category.

Figure 9:
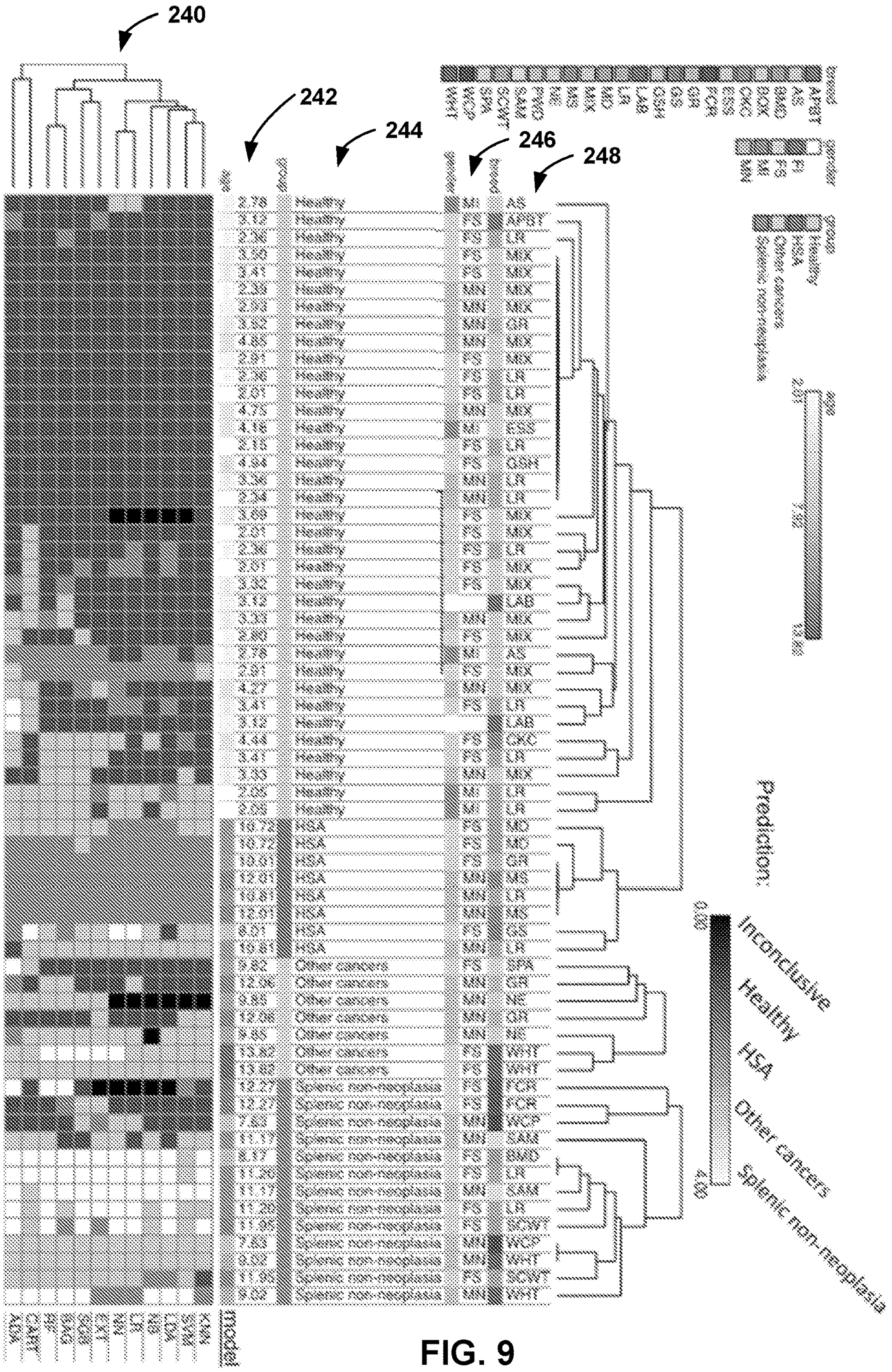
FIG. 9 is a matrix illustrating the relationship between classifications and characteristics of subjects from which different samples were obtained.

FIG. 9 is a matrix illustrating the relationship between classifications and characteristics of subjects from which different samples were obtained. As shown in the example of FIG. 9, the relationship between categorical assignments 244 from machine learning algorithms 240 with breed 248, gender 246, or age 242 in the training set. Predictions for dogs with confirmed diagnoses of HSA or any other cancer ("other cancers") are visualized on a matrix displaying breed, gender (including neuter or hormonal status), and age. When multiple samples were obtained for a dog, they were considered individually and are so represented in FIG. 9. The difference in age between the "healthy" dog group and the other three groups is by design. There is otherwise no correlation between breed and diagnosis, or between gender (or hormonal status) and diagnosis. FIG. 9 indicates the overall accuracy of predictions and the degree of agreement among machine learning algorithms 240.

Figure 10:
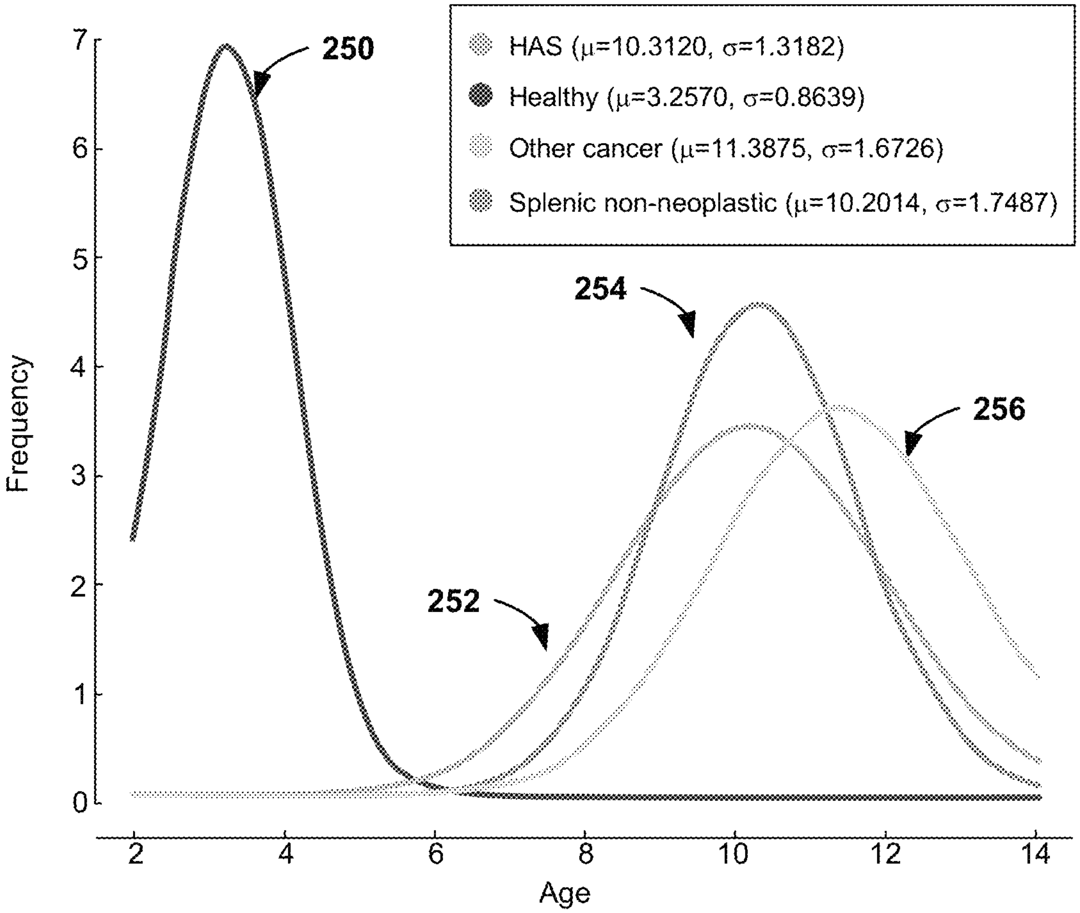
FIG. 10 is a graph illustrating the relationship between number of subjects and age for different classifications for different samples.

FIG. 10 is a graph illustrating the relationship between number of subjects and age for different classifications for different samples. As shown in FIG. 10, a relationship between categorical assignments from machine learning algorithms with breed, gender, or age in the training set is shown. FIG. 10 illustrates the distribution of age by group. The age of every dog in each group is plotted as a function of age, showing the mean age and the standard deviation in the box.

Figure 11:
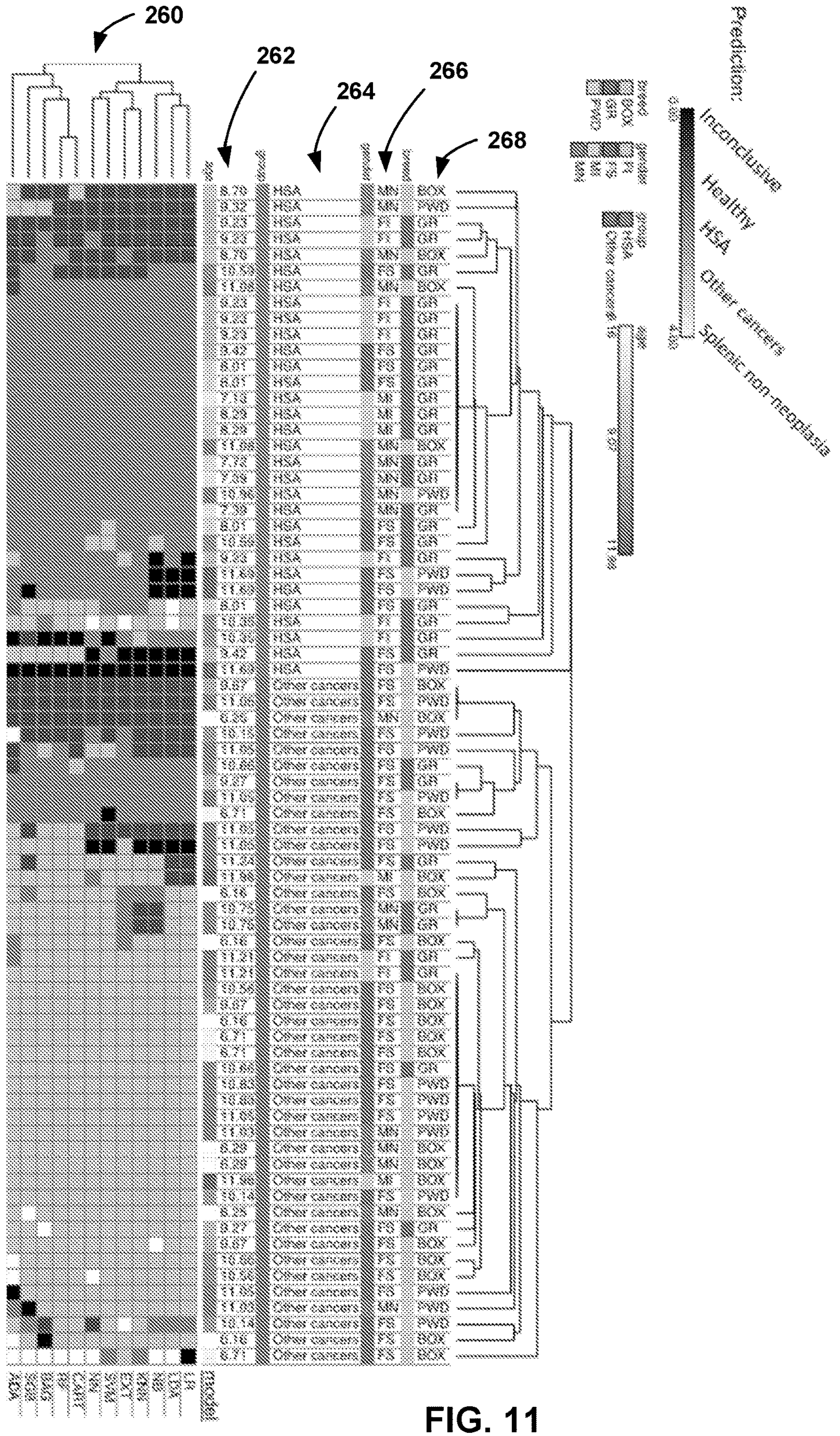
FIG. 11 is a matrix illustrating the relationship between classifications and characteristics of subjects from which different samples were obtained.

FIG. 11 is a matrix illustrating the relationship between classifications and characteristics of subjects from which different samples were obtained. As shown in FIG. 11, the relationship between categorical assignments 264 from machine learning algorithms 260 with breed 268, gender 266, or age 262 in the test set. The predictions for dogs with confirmed diagnoses of HSA or any other cancer ("other cancers") are visualized on a matrix displaying breed, gender (including neuter or hormonal status), and age. When multiple samples were obtained for a dog, they were considered individually and are so represented in FIG. 11. There is no correlation between breed and diagnosis, or between gender (or hormonal status) and diagnosis. The overall accuracy of predictions and the degree of agreement among algorithms is high as shown in FIG. 11.

Figure 12:
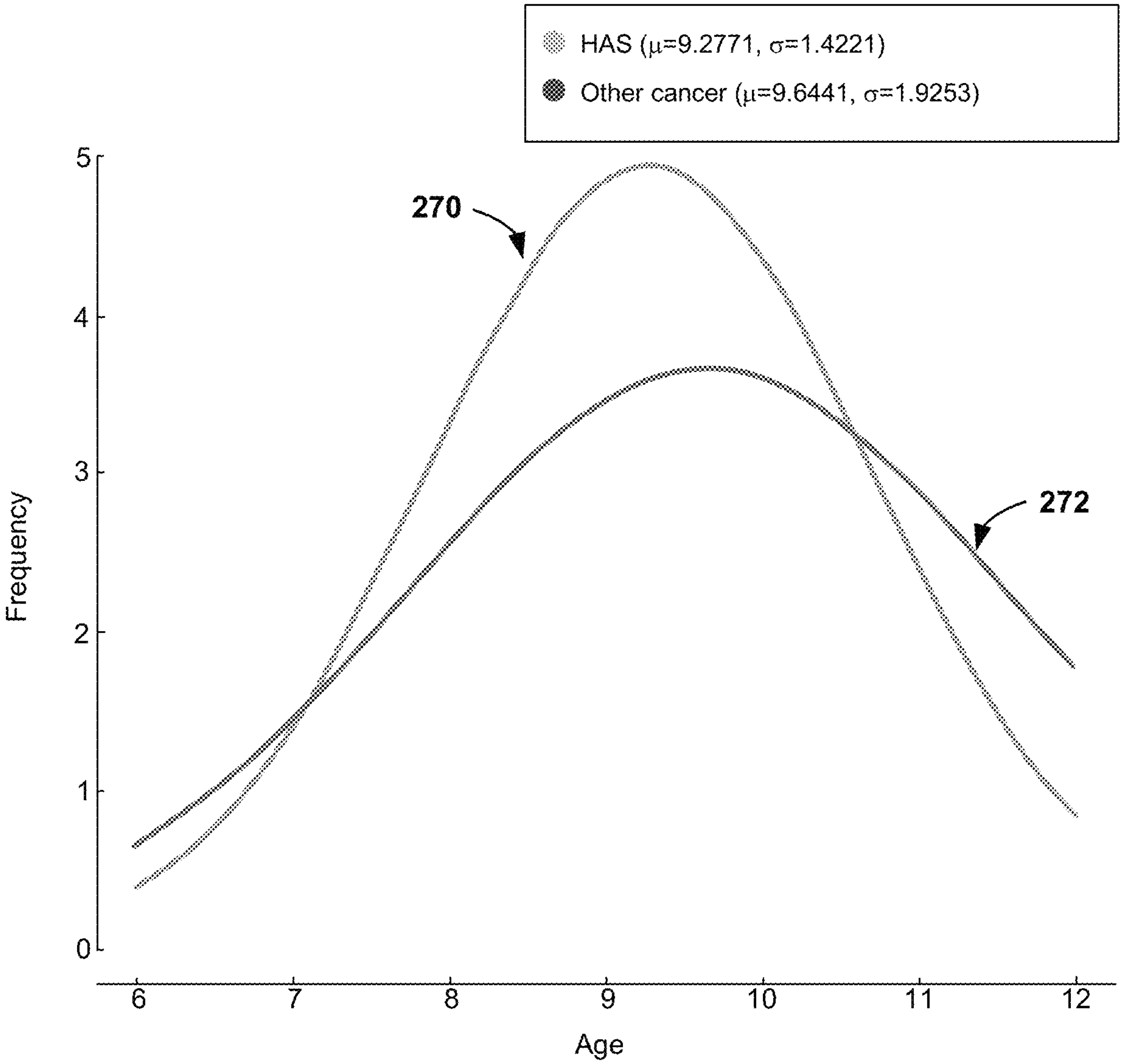
FIG. 12 is a graph illustrating the relationship between number of subjects and age for different classifications for different samples.

FIG. 12 is a graph illustrating the relationship between number of subjects and age for different classifications for different samples. As shown in FIG. 12, the relationship between categorical assignments from machine learning algorithms and breed, gender, or age in the test set is provided and shown as a distribution of age by group. The age of every dog in the HSA and Other cancer groups is plotted as a function of age, showing the mean age and the standard deviation in the box. Healthy dogs and dogs with benign vascular pathology (splenic non-neoplasia) are not included in this figure.

Figure 13:
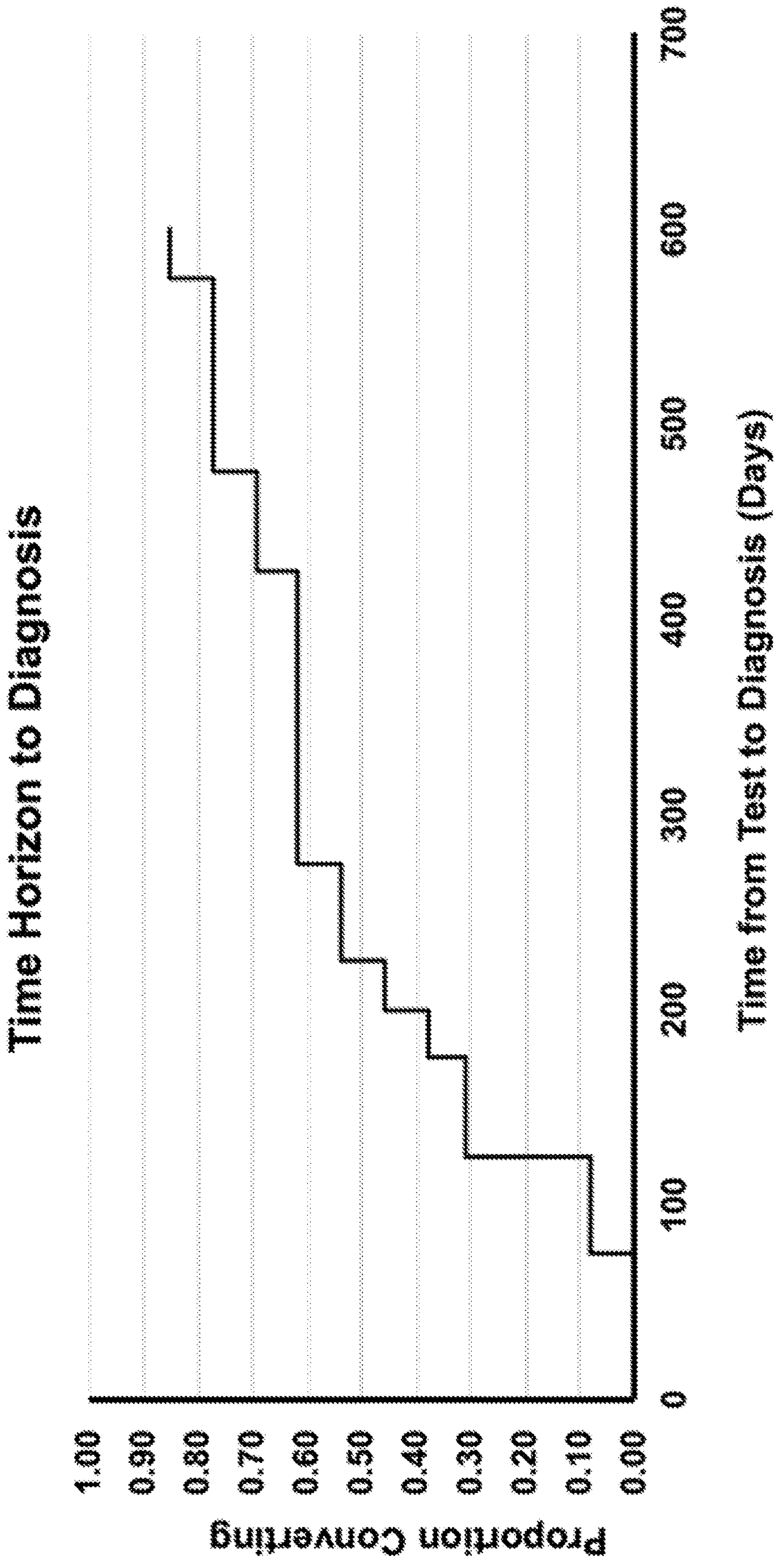
FIG. 13 is a graph illustrating the duration of time for disease to develop after initial screening and classification described herein.

FIG. 13 is a graph illustrating the duration of time for disease to develop after initial screening and classification described herein. A question to be considered for any early detection test (e.g., a screening test) is the time horizon to disease development. In other words, how many subjects that develop the condition in question were correctly predicted to be "at risk" for that condition. This defines the observed sensitivity, or true positive rate for the assay. As shown in FIG. 13, the data for dogs that were diagnosed with HSA (according to the machine learning algorithms) is plotted against time, showing the overall sensitivity of the test to detect true positives over a 2-year period. Fifteen dogs that were enrolled in the study were diagnosed with and/or died of HSA. The test correctly predicted risk for HSA in 13 of the dogs (87%), with the interval from testing to diagnosis ranging from approximately 60 to over 600 days.

Figure 14A:
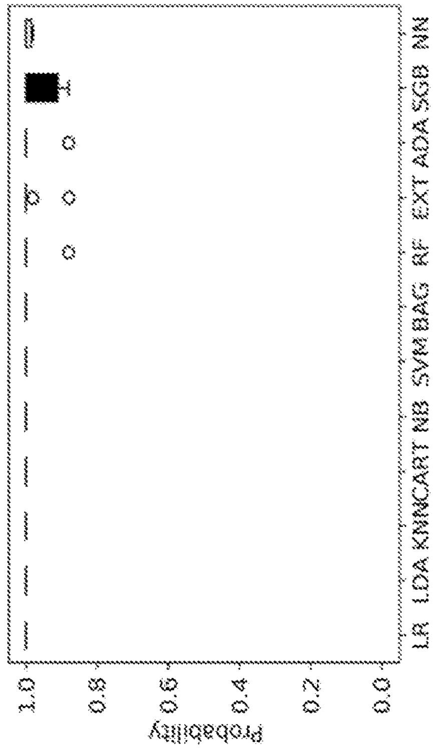
FIGS. 14A, 14B, 14C, and 14D are graphs of example machine learning performance using different features from data.
Figure 14B:
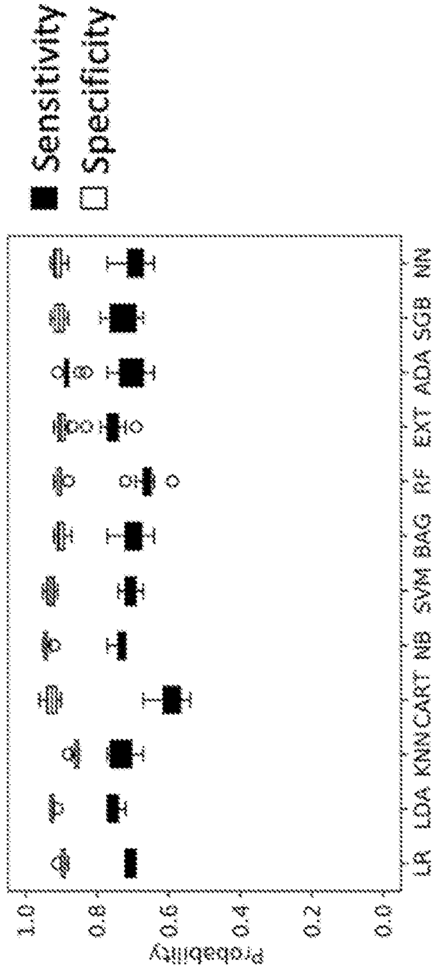
Figure 14C:
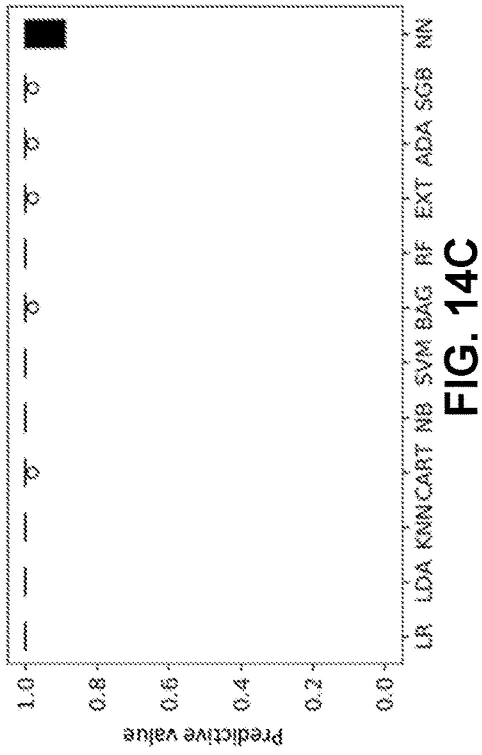
Figure 14D:
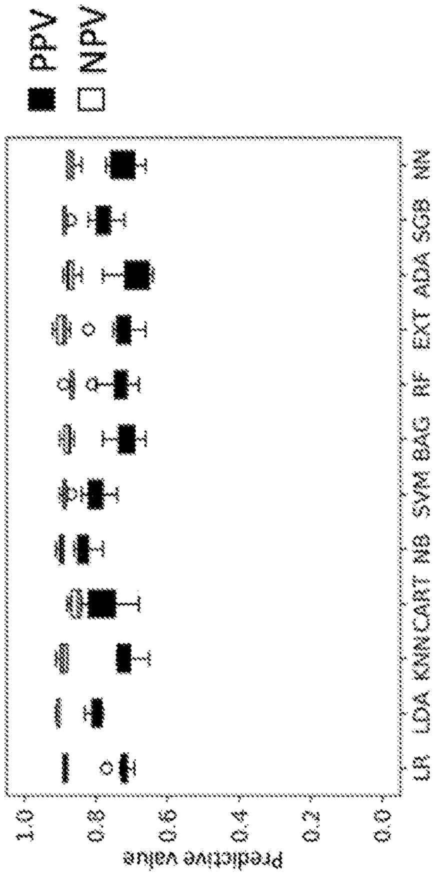

FIGS. 14A, 14B, 14C, and 14D are graphs of example machine learning performance using different features from data. Machine learning performance can be determined for each algorithm when adding data from dogs diagnosed with early disease. The training set for the machine learning algorithms used dogs with confirmed diagnoses of HSA, other tumors, or benign vascular pathology. Here, data from dogs that were presumably healthy at the time of testing, and later developed disease that allowed them to be classified into one of the three pathological categories in the subsequent 2-years after testing, were added. As shown in FIG. 14A, the box and whiskers probability plot shows sensitivity (true positive rate, filled boxes) and specificity (true negative rate, clear boxes) for 12 distinct machine learning algorithms using training and 10 random iterations of 10-fold cross validation with LDA-transformed 42 features, using exclusively the data from dogs with active disease. FIG. 14B illustrates performance of the assay when data are added from dogs that were presumably healthy at the time of testing but were subsequently diagnosed with a condition within a 2-year interval. FIG. 14C illustrates a positive predictive value (probability that subjects with a positive screening test truly have the disease, filled boxes) and negative predictive value (probability that subjects with a negative screening test truly don't have the disease, clear boxes) of the assay for 12 distinct machine learning algorithms using training and repeated 10-fold cross validations as above with LDA-transformed 42 features using exclusively the data from dogs with active disease. FIG. 14D illustrates a positive predictive value and negative predictive value of the assay when data are added from dogs that were presumably healthy at the time of testing but were subsequently diagnosed with a condition within a 2-year interval.

Figure 15A:
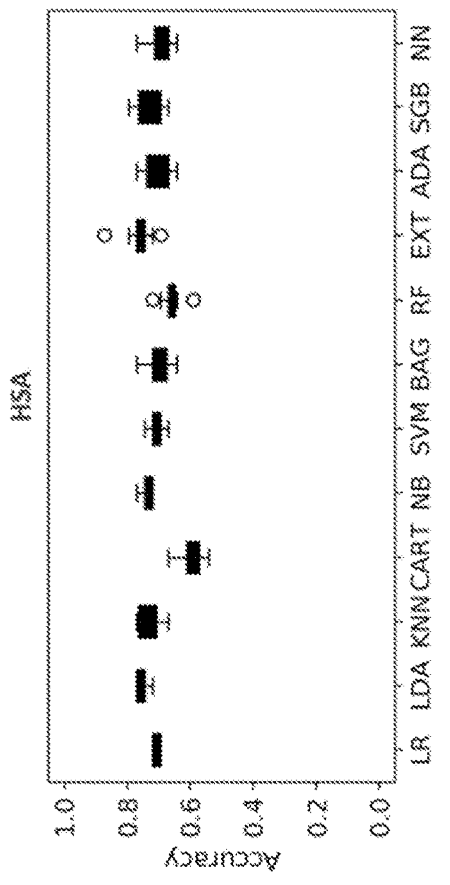
FIGS. 15A, 15B, 15C, and 15D are graphs of example machine learning accuracy for different classifications of samples.
Figure 15B:
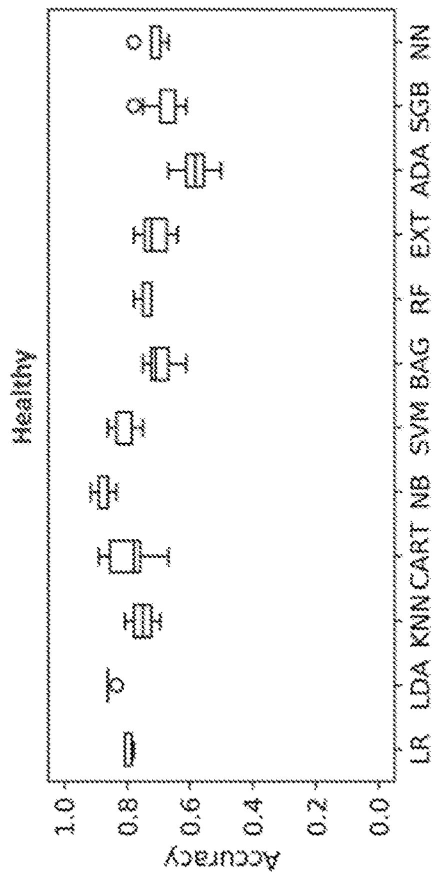
Figure 15C:
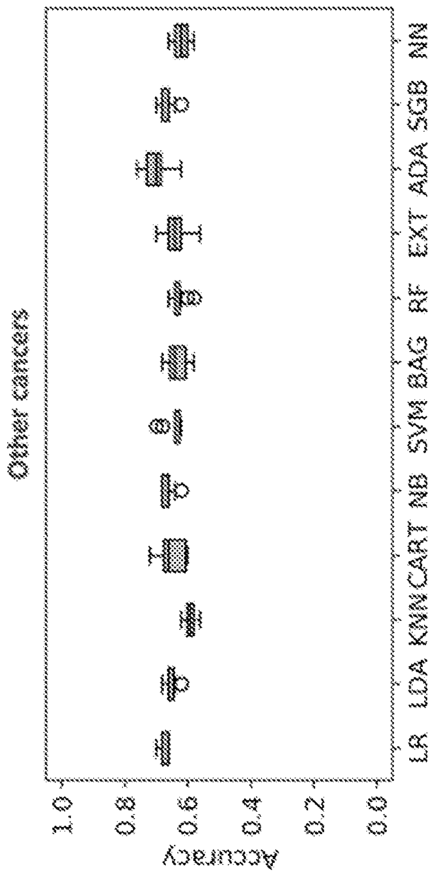
Figure 15D:
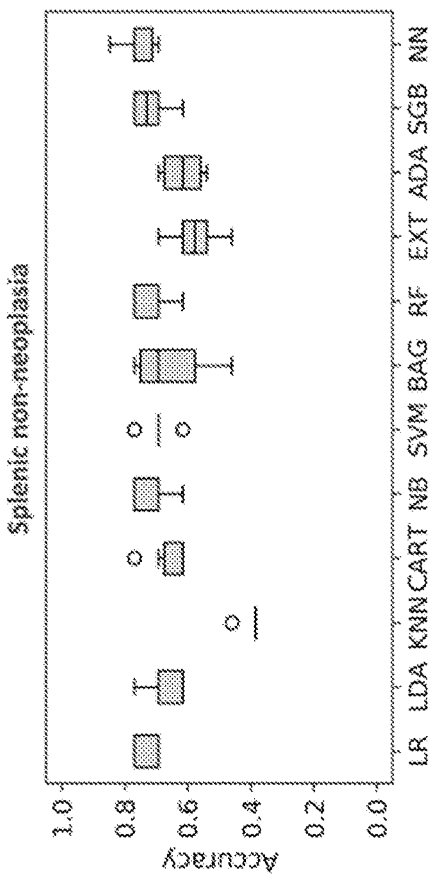
Figure 16:
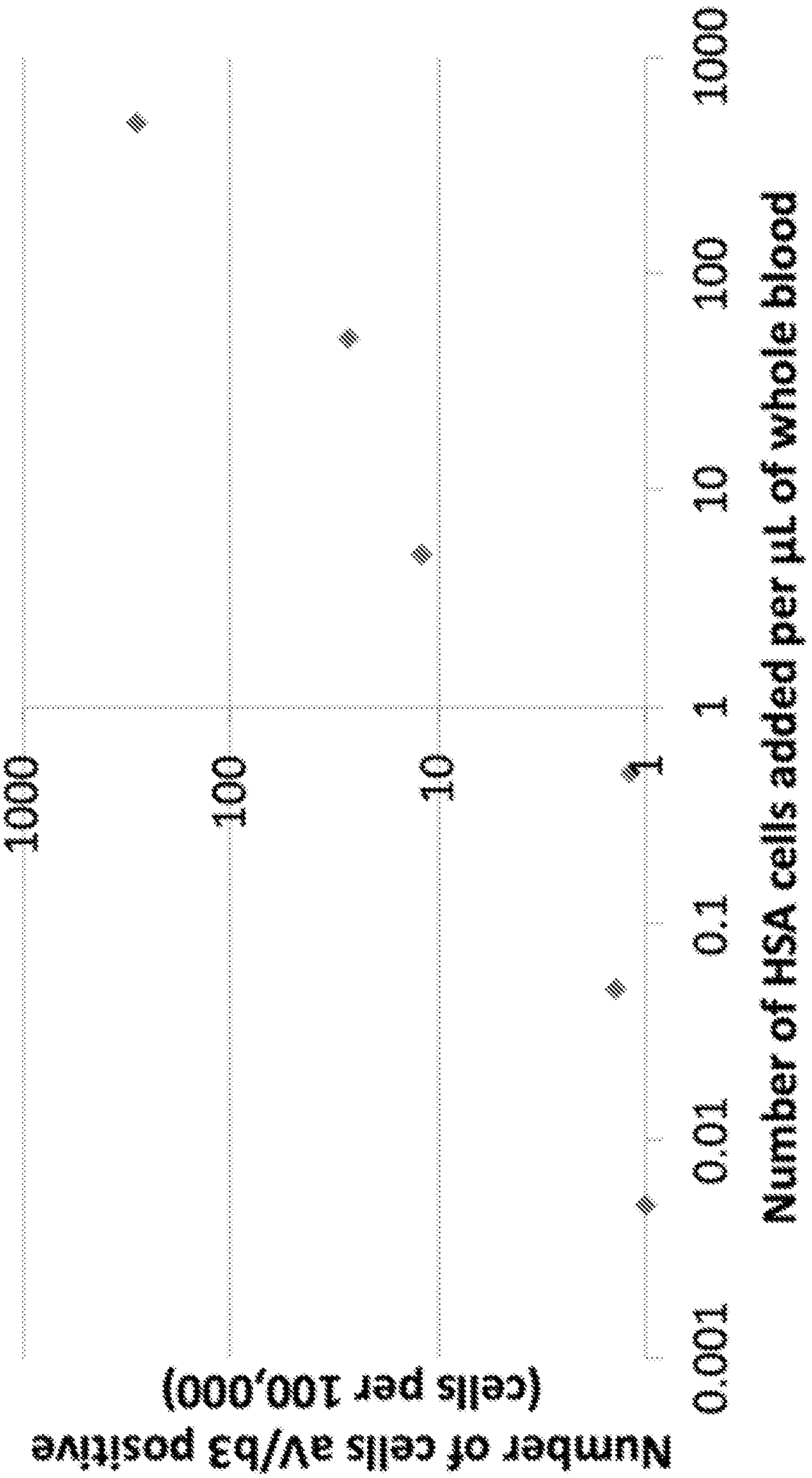
FIG. 16 is a graph illustrating a lower level of detection for number of HSA cells tested.

FIGS. 15A, 15B, 15C, and 15D are graphs of example machine learning accuracy for different classifications of samples. These figures illustrate a summary of LDA transformed 42-feature machine learning classification accuracy for assignment of canine samples into HSA, other cancers, benign vascular pathology, or presumably healthy categories when adding data from dogs diagnosed with early disease. Box and whiskers probability plots showing the classification accuracy (the accuracy of prediction) for each category across 12 distinct machine learning algorithms using training and 10 random iterations of 10-fold cross validation with 42 features when data are added from dogs that were presumably healthy at the time of testing but were subsequently diagnosed with a condition within a 2-year interval (data from FIGS. 14A-14D). FIG. 15A illustrates the classification accuracy for the HSA category and FIG. 15B illustrates the classification accuracy for presumably healthy category. FIG. 15C illustrates the classification accuracy for other cancer category, and FIG. 15D illustrates the classification accuracy for benign vascular pathology ("splenic non-neoplasia") category.

In some examples, the techniques described herein may add antibodies to exclude CD5+, CD11b+, and CD22+ cells and to enrich cells expressing CD34, CD117, and CD51/61 by flow cytometry. A lower limit of detection for circulating HSA associated cells (FIG. 16) can be established by spiking cultured HSA cells into normal blood, prior to processing, and then evaluating samples, as shown in FIG. 1A and FIGS. 2A-2E. HSA cells were identified based on co-expression of CD34/CD117 and $\alpha_v\beta_3$-integrin (quadrant-2 in the example shown in FIG. 2E). This establishes a performance metric for the flow cytometer and for the technique of flow cytometry. However, CTCs and/or CTACs can be enumerated to within this limit of detection in blood samples from dogs with HSA (n=13), splenic hematoma (n=8), cancer other than HSA (n=23), and no known disease (n=25). Some parameters may exclude monocytes, platelets, or all leukocytes, as well as to detect co-expression of the hyaluronic acid receptor (CD44). Single cell sequencing data (FIGS. 17-21D) indicates that at least some of the cells captured by the assay, and in particular, those found in quadrants-1 and -3, represent HSA-associated cells that are likely mobilized as part of the formation and/or maintenance of the tumor niche. The presence of circulating tumor cells appears to be quite variable, and in most samples of dogs with HSA, events in quadrant-2 are infrequent.

The results of such a test may enable identification of as few as 1-5 HSA cells (CTCs) and/or CTACs per 100,000 nucleated cells in blood from apparently healthy dogs. In some examples, a statistical significance test (e.g., Fisher's exact test) can be applied to the data to illustrate which combinations of classifications were significantly different from each other when classifying these four groups using simple statistics considering only single or dual parameters established from flow cytometric markers. Canine platelets expressed CD51/61 and CD44, but not CD45 and canine HSA cells expressed CD41/CD61. Cells co-expressing CD51/CD61 with CD34 and/or CD117 were not detected in canine blood samples; however, CD51/CD61+ cells were significantly more prevalent in dogs with HSA than in healthy dogs and in dogs with cancer other than HSA. In this manner, CD51/CD61+ cells are detectable in blood of dogs with HSA using flow cytometry. However, the improvement on the detection achieved by incorporating additional features and machine learning are evident from Table 1 and Table 2 and the data shown in FIGS. 4D-4F and elsewhere described herein.

Figure 17:
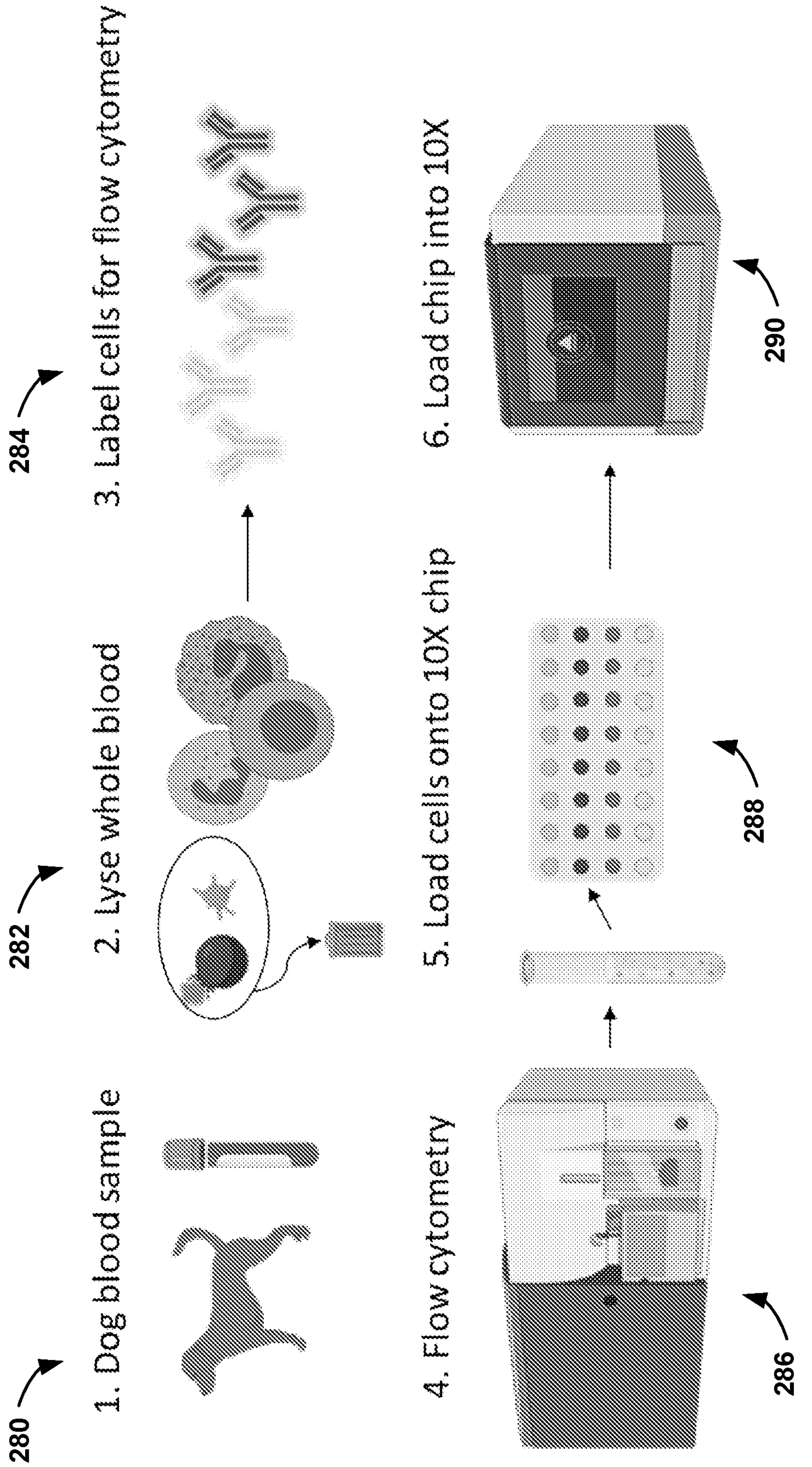
FIG. 17 is a schematic diagram illustrating an example process for single cell sequencing.

FIG. 17 is a schematic diagram illustrating an example process for single cell sequencing. The process of FIG. 17 will be described with respect to performance by a technician, but any user or system may perform this process in other examples. As shown in FIG. 17, step 280 involves the technician obtaining blood samples from dogs with confirmed HSA (active disease or minimal residual disease). In step 282, the technician may subject the blood samples to hypotonic lysis to eliminate erythrocytes (RBCs) and deplete platelets. In step 284, a technician may mark the remaining leukocytes with antibodies to establish a single color "dump gate" to exclude T cells (CD5), B cells (CD22), and myeloid cells/granulocytes (CD11b). Circulating HSA-associated cells are marked with specific antibodies that recognize $\alpha_v\beta_3$-integrin and hematopoietic progenitor markers CD34 and CD117 and $\alpha_v\beta_3$-integrin. In step 286, a technician may sort the samples using a multi-parameter fluorescence activated cell sorter (FACS). In step 288, the technician may bar-code sorted cells and load the cells onto a 10× single cell sequencing chip for analysis. Any single cell sequencing platform may perform this analysis, such as systems by Fluidigm or BD Biosciences. In step 290, a technician may perform sequencing using established 10× protocols.

Figure 18:
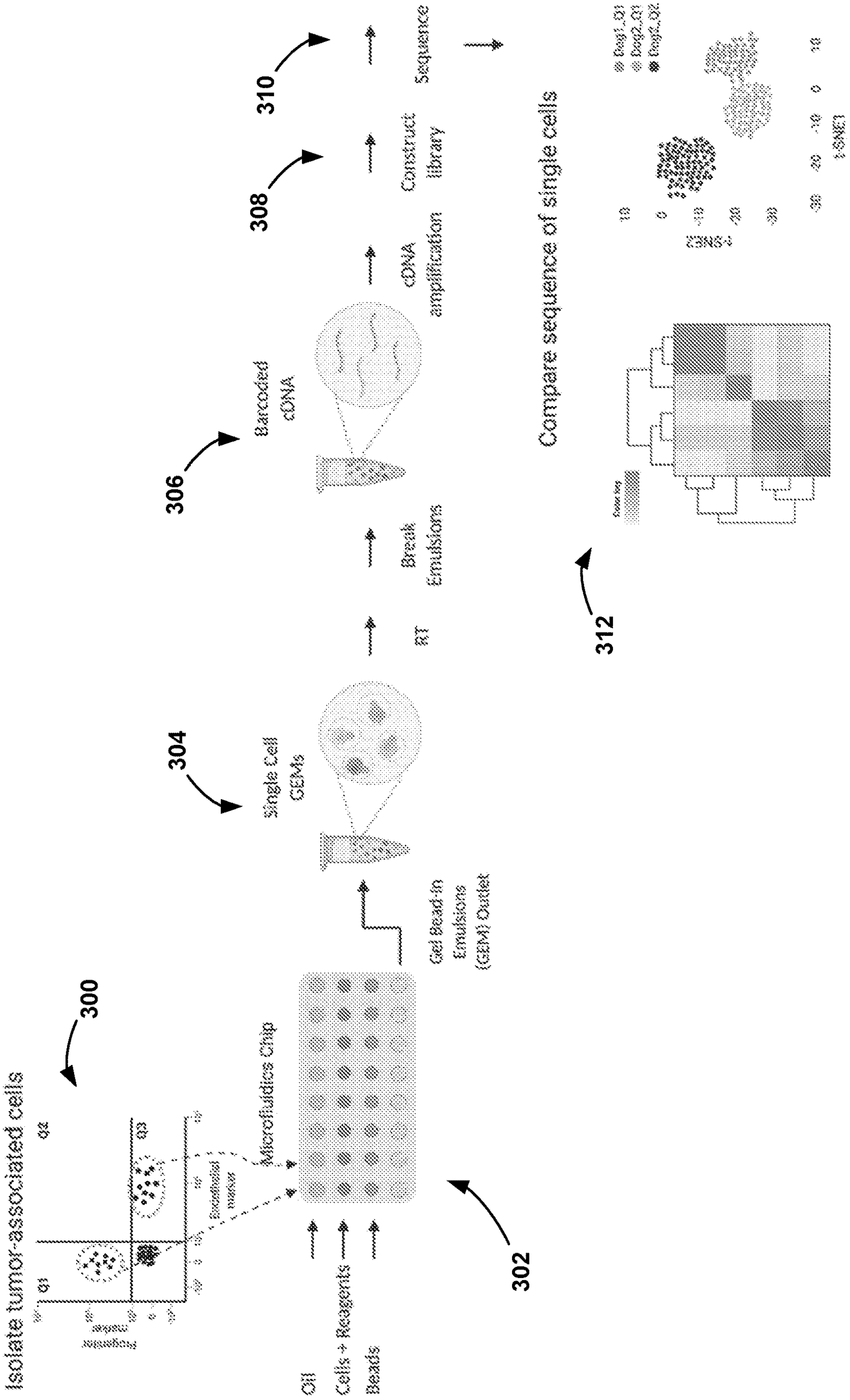
FIG. 18 is a schematic diagram illustrating an example process for single cell sequencing and analysis.

FIG. 18 is a schematic diagram illustrating an example process for single cell sequencing and analysis. As shown in FIG. 18, events from the desired quadrants are captured by cell sorting (step 300). Cells are then loaded directly from the sorter into a 10× microfluidics chip (step 302). In this example, cells are sorted according to expression of CD34/CD117 ("progenitor markers") and $\alpha_v\beta_3$-integrin ("endothelial marker"). Events from quadrant-1 and from quadrant-3 are captured into the assay as cells of interest. In this example, events from quadrant-2 are insufficient for analysis. In step 304, the cells pass through the 10× microfluidic chip and are captured as single events in a Gel Bead-in emulsion (GEM). In step 306, RNA is isolated and subjected to reverse transcription (RT). The emulsions are disrupted and cDNAs are barcoded for subsequent identification and assignment to individual cells. The cDNA undergoes amplification using polymerase chain reaction (PCR) to build the sequencing libraries. Sequencing is then performed by a next generation sequencer (step 310). A system or technician may then perform bioinformatics analysis as described herein to cluster the cells and assign lineages.

Figure 19:
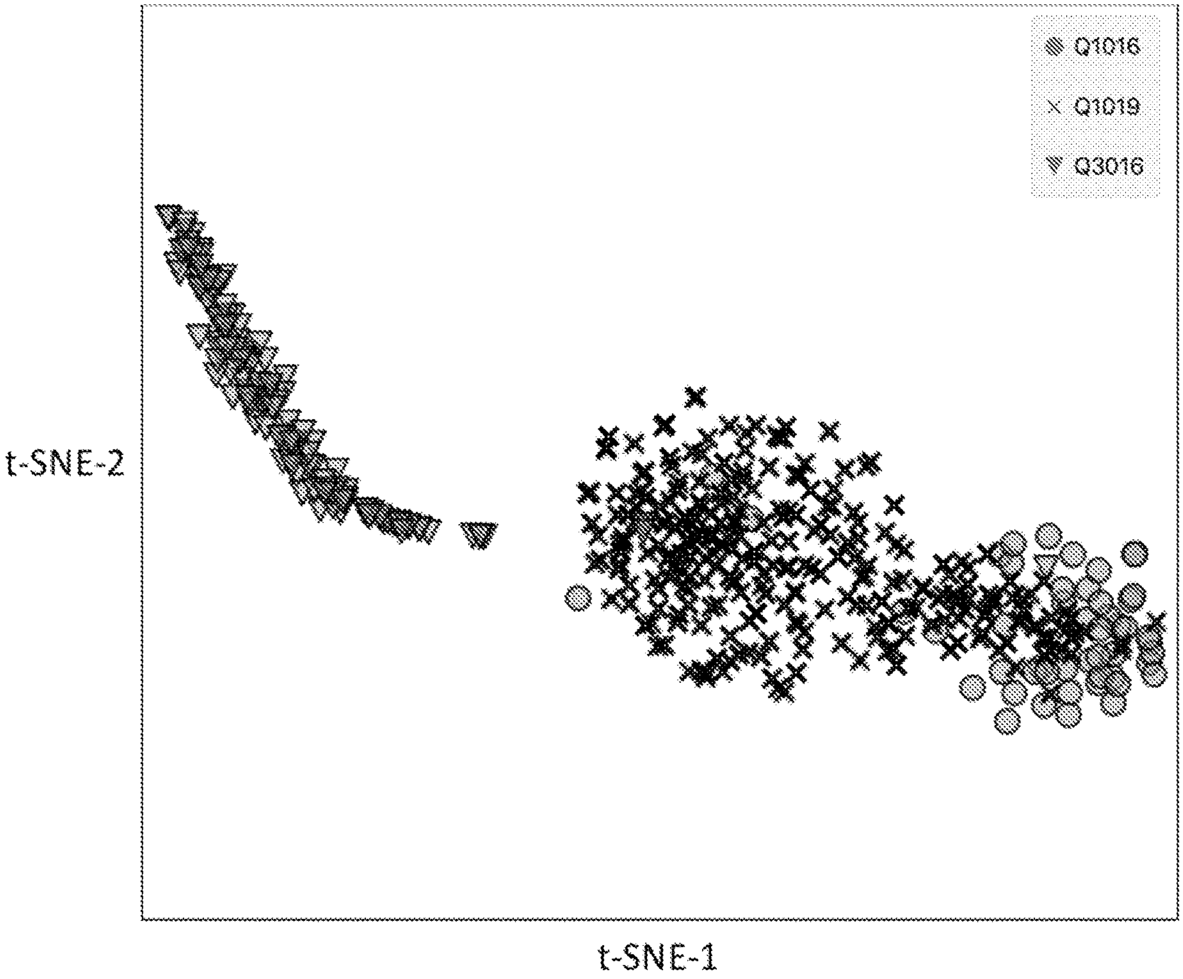
FIG. 19 is a graph illustrating example clustering of single-cells according to expression profiles.

FIG. 19 is a graph illustrating example clustering of single-cells according to expression profiles. Data features generated by the single cell sequencing may include indications of the expression profiles of the cells. Samples from two dogs subjected to single cell sequencing as described in FIGS. 9 and 10 are shown on a t-SNE plot. One sample had sufficient events for RNA-seq in quadrant-1 (CD34/CD117; Q1016) and in quadrant-3 ($\alpha_v\beta_3$-integrin; Q3016). The other dogs only had enough events for RNA-seq in quadrant-1 (Q1019). The data show comparable clustering of events captured from Q1 in both dogs, separated from events captured in Q3 from subject 016 using all 4,735 detected genes.

Figure 20A:
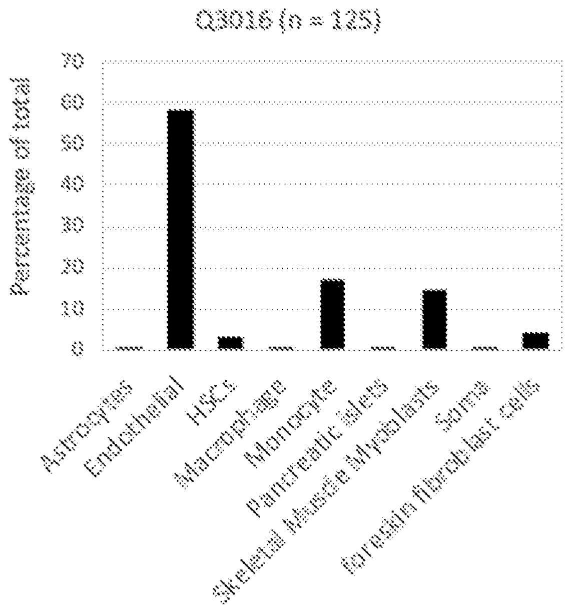
FIGS. 20A, 20B, and 20C are graphs illustrating example identifications of cells based on single cell RNA sequencing.
Figure 20B:
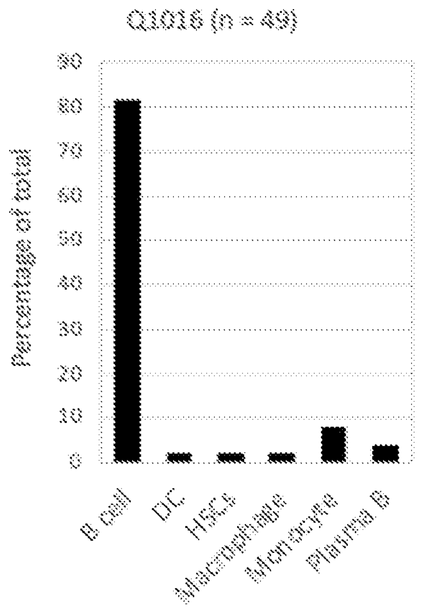
Figure 20C:
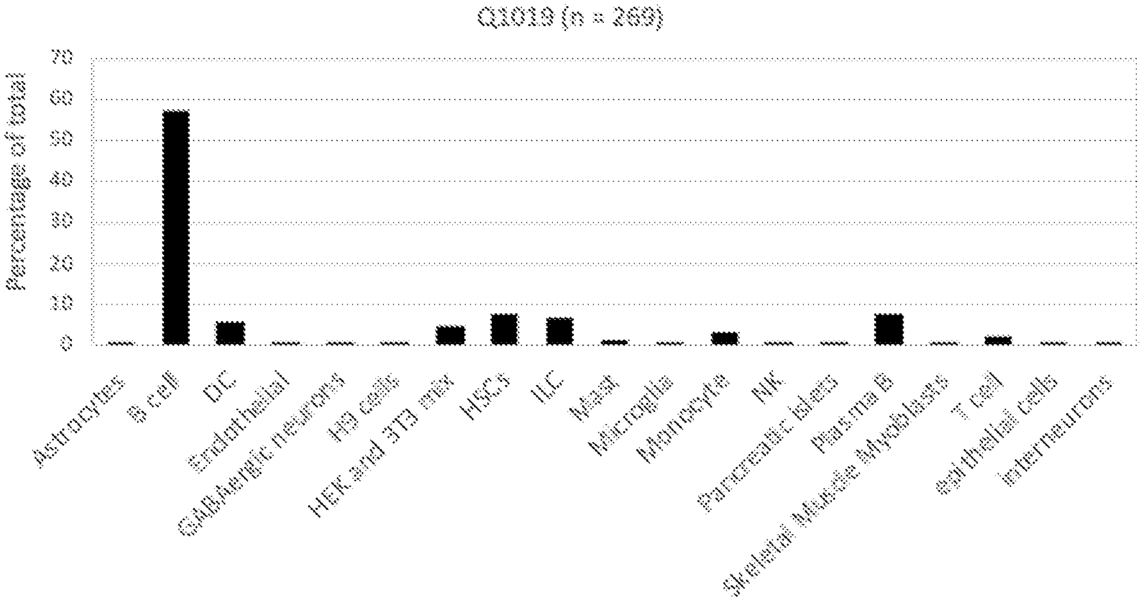

FIGS. 20A, 20B, and 20C are graphs illustrating example identifications of cells based on single cell RNA sequencing. Sequencing data from the experiment described in FIG. 19 were used to assign a presumptive lineage of origin to each cell. The SciBet package was used to integrate the complement of genes for each event and predict its lineage. FIG. 20A illustrates the percentage of cells captured in quadrant-3 from subject 016 represented a variety of stromal or mesenchymal lineages, including endothelial cells, myoblasts, monocytes, and fibroblasts. All of these cells are involved with formation of vascular networks in the tumor niche. FIG. 20B illustrates the percentage of total cells captured in quadrant-1 from subject 016 represented a variety of lymphoid and other hematopoietic cells, including B cells, plasma cells, and monocytes. FIG. 20C illustrates the percentage of total cells captured in quadrant-1 from subject 019 represented a variety of lymphoid and other hematopoietic cells, including B cells, plasma cells, hematopoietic stem cells, and innate lymphoid cells. The fact that cells in quadrant-1 for both subjects were captured using a combination of progenitor markers (CD34 and CD117) indicates that these are not "conventional" mature leukocytes and are likely to represent progenitor or incompletely differentiated cells or blasts. In this example, it is likely that these cells contribute to the formation of the tumor niche, and they are clearly important in the final assignment of samples to a risk category (HSA, other cancer, benign vascular lesion, or apparently healthy). However, it may be possible that these events are not excluded by the gating strategy and the antibody panel used for the dump gate.

FIGS. 21A, 21B, 21C, and 21D are graphs illustrating a screening test for HSA associated cells before and after preventative treatment. The utility of any diagnostic test may be intimately tied to its actionability. The usefulness of the test described herein in the early detection and prevention setting by providing a dog assigned to the category of "positive risk for HSA" with a preventative treatment using the drug eBAT. The figures include two-dimensional forward and side scatter flow cytometry dot plots representing the terminal gating for $\alpha_v\beta_3$-integrin (CD51/CD61)+ cells from the CD34/c-Kit/$\alpha_v\beta_3$-integrin staining condition (FIG. 21A) and the terminal gating for CD44+/$\alpha_v\beta_3$-integrin+ cells (FIG. 21B) from the first HSA detection test (see FIGS. 2A-2E for example procedure description). In addition, the figures include two-dimensional forward and side scatter flow cytometry dot plots representing the terminal gating for $\alpha_v\beta_3$-integrin (CD51/CD61)+ cells from the CD34/c-Kit/$\alpha_v\beta_3$-integrin staining condition (FIG. 21C) and the terminal gating for CD44+/$\alpha_v\beta_3$-integrin+ cells (FIG. 21D) from the HSA detection test done 3 months after the dog received eBAT. Note the number of HSA-associated cells, which was stable during the initial screens, was reduced by two orders of magnitude after eBAT preventative treatment.

FIGS. 22A, 22B, and 22C are cytograms of the side and forward angle light scatter (SS and FS) from cells pre- and post-treatment to monitor duration of remission. Here, the figures illustrate the usefulness of the described screening test for HSA by monitoring the presence of events that define "risk" at serial intervals after standard of care treatment. As shown in FIG. 22, flow cytometry indicates the presence of CTCs and/or CTACs in a subject known to have HSA. FIG. 22A illustrates two-dimensional forward and side scatter flow cytometry dot plots representing the terminal gating for $\alpha_v\beta_3$-integrin (CD51/CD61)+ cells from the CD34/c-Kit/$\alpha_v\beta_3$-integrin staining condition on the day of diagnosis and before treatment. Events in the diagnostic gate marked with a circle are detected (see FIGS. 2A-2E for the procedure description). FIG. 22B includes two-dimensional forward and side scatter flow cytometry dot plots representing the terminal gating for $\alpha_v\beta_3$-integrin (CD51/CD61)+ cells from the CD34/c-Kit/$\alpha_v\beta_3$-integrin staining condition 60 days after treatment, while the dog remains in clinical remission. Note the virtual absence of cells in the diagnostic gate marked with a circle. FIG. 22C includes two-dimensional forward and side scatter flow cytometry dot plots representing the terminal gating for $\alpha_v\beta_3$-integrin (CD51/CD61)+ cells from the CD34/c-Kit/$\alpha_v\beta_3$-integrin staining condition 120 days after treatment, while the dog remains in clinical remission. Note the slight increase of cells in the diagnostic gate marked with a circle, suggesting the dog may be at risk for relapse. Therefore, after treatment, the day 60 post-treatment (FIG. 22B) and day 120 post-treatment (FIG. 22C) samples illustrate a reduction in the detected CTCs and/or CTACs when compared with the initial analysis before treatment. Furthermore, the day 120 post-treatment (FIG. 22C) sample illustrates increasing presence of CTCs and/or CTACs in the same subject, documenting increasing risk of relapse. Therefore, the techniques described herein may enable monitoring of residual disease, allowing for potential alterations in treatment to maintain remission, as well as early detection and treatment for a subject that may otherwise not have been treated for HSA.

Cancers other than HSA may vary for the type of subject tested. In some examples, cancers other than HSA, as classified and described herein, may include one or more of lymphoma, osteosarcoma, melanoma, chondrosarcoma, gastric adenocarcinoma, mast cell tumors, transitional cell carcinoma, peripheral nerve sheath tumor, meningioma, leiomyosarcoma, mammary carcinoma, splenic stromal sarcoma, and/or spindle cell sarcoma.

As discussed herein, the techniques may include obtaining and preparing blood samples, running each sample through flow cytometry to obtain associated measurements and data features, training analytical models, and then classifying each sample according to the classifications from a plurality of the trained analytical models.

Peripheral blood samples from healthy dogs, or from dogs with confirmed diagnoses of HSA, other cancers, or benign vascular pathology may first be collected into 3-mL EDTA vacutainer tubes using a butterfly extension. Blood samples can be processed for staining using routine protocols. Briefly, nucleated cells can be enriched through a red cell lysis step to deplete red blood cells and platelets. The remaining nucleated cells can be resuspended in blocking buffer (PBS, 0.2% fetal bovine serum, and 10 μg mouse IgG and/or canine IgG) and incubated at 4° C. for 10 minutes, after which fluorescently labeled antibodies were added in the following combinations: (1) $\alpha v\beta_3$-integrin, CD5, CD11b, CD22, CD34, and c-kit, live/dead stain; (2) $\alpha v\beta_3$-integrin, CD5, CD11b, CD22, CD45, live/dead stain; (3) $\alpha v\beta_3$-integrin, CD5, CD11b, CD22, CD45, CD44, live/dead stain; and (4) $\alpha v\beta_3$-integrin, CD5, CD11b, CD22, CD44, live/dead stain. Additional markers incorporated into these steps based on predictions from gene expression and lineage tracing include CD14, CD18, CD11/CD18, CD41/CD61 ($\alpha_2\beta_3$-integrin), CD105, CD146, CD31, Tie1, Tie2, VEGFR1, VEGFR2, PDGFRα, and PDGFRβ, among others. Other markers may include CD14, CD3, NKp46, CD8, CD21, CD20, and/or CD22. These markers may be used as part of the dump gate described herein and/or for single color labeling for each antibody to manipulate the dump gate more precisely.

Unstained controls, isotype controls, and single stained or bead-based compensation controls can be included for each combination and each sample. Cells were incubated for 30 minutes at 4° C. protected from light, washed three times in staining buffer (PBS, 0.2% fetal bovine serum, 2 mM EDTA, 0.05% NaN3) and fixed in 2-2.5% formalin. Flow cytometry can be done using any multiparameter flow cytometer, such as a BD LSR II instrument, a BD FACS Celesta, or a BD FACSLyric, and data may be analyzed using analysis software such as FlowJo v10. For analysis, an iterative gating strategy can be used to (1) include leukocytes and exclude debris using light scatter, (2) exclude doublets using forward scatter height and amplitude or side scatter side and amplitude, (3) exclude dead cells using a live/dead stain, and (4) exclude normal leukocytes using a one-color or a multi-color "dump gate," for example, where a one-color dump gate is established by use of FITC-labeled anti-CD5, anti-CD11b, and anti-CD22, +/−anti-CD45+/−CD14. The remaining non-white blood nucleated cells are analyzed to identify events expressing $\alpha v\beta_3$-integrin, CD34, c-kit, CD44, and CD45, individually and in combination. Data features were exported into text-delimited files for machine learning.

In the Data Analysis and Machine Learning process, all of the relevant features extracted from flow cytometric measurements can be used in the analysis. As one example, eleven such data features can include normalized counts for: (1) Quadrant-1 (Q1) progenitors (CD34+/c-Kit+), (2) Q2 double positive (CD34+/c-Kit+/$\alpha v\beta_3$-integrin+), (3) Q3_avb$_3$ ($\alpha v\beta_3$-integrin+), (4) Q3 SS high (high complexity−Side Scatter>100), (5) Q3 SS low (low complexity−Side Scatter<100), and $\alpha v\beta_3$-integrin fluorescence intensity (FI) data from negative (Q4) and positive (Q3) populations that include: (6) total FI (normalized to 100,000 leukocytes), (7) relative mean FI, (8) relative median FI, (9) standard deviation of FI, (10) relative minimum FI, and (11) relative maximum FI. Relative data measurement indicates relative to the mean FI of the negative Q4 population.

To determine data quality, data from healthy dogs, dogs with benign vascular pathology (Splenic non-HSA), dogs with other cancers, and dogs with HSA can be first analyzed using all such 11 data features described above by unsupervised principal component analysis (PCA) and k-means clustering (k-Means), and by supervised linear discriminant analysis (LDA). Data with missing one or more feature values and/or with inconclusive diagnostic data may be excluded for machine learning model development and training.

Feature selection may be performed to determine the optimal feature combination(s) for the best classification by different machine learning models. Top feature combination(s) were chosen based on seven different statistical scoring methods—Information Gain, Gain Ratio, Gini, ANOVA, Chi-squared, ReliefF, and Fast Correlation Based Filter (FCBF) docs.biolab.si//3/visual-programming/widgets/data/rank.html)—and by brute force feature selection (specific to top models selected below). Each feature combination selected might be common across different machine learning models (e.g., analytical models), or it might be model-specific.

Different machine learning algorithms (e.g., analytical models) were used initially to build different models for optimization and training, including Logistic Regression (LR), Linear Discriminant Analysis (LDA), k-nearest neighbors (kNN), Classification and Regression Trees (CART), Neural Network (NN), Support Vector Machine (SVM), Random Forest (RF), Decision Tree Classifier (Tree), Adaptive Boosting (AdaBoost or ADA), Extra Trees Classifier (EXT), Bagging (BAG), Gaussian Naïve Bayes (NB), Stochastic Gradient Boosting (SGB), and Deep Learning (DL) algorithms. More or fewer analytical models may be used in other examples. K-fold cross-validations can be performed and compared across all analytical models using all features as well as different feature combinations identified based on scoring methods described above. K-fold cross-validation randomly splits data into k number of training and validation sets for model testing. Top three models with the best averaged test scores, including area under curve (AUC), classification accuracy (CA), F1, and log loss, can be chosen. However, one or two models may be chosen in other examples, or four or more analytical models may be chosen in alternative examples. Comparable performance for classification accuracy, for example, small standard deviation among top-8 algorithms as described above, provides confidence in the quality of data and training.

All currently available data from the subjects passing quality control (QC) were used to train the top models. As new unknown samples are received, they can be subjected to QC and classified using the trained machine learning models. For example, in training three models, samples receiving a minimum of ⅔ healthy, Splenic non-HSA, Other cancers, or HSA calls (2 models out of 3, or the majority of the analytical models) will be classified accordingly. Samples receiving ⅓ mixed calls (inconsistent in all 3 models) may be considered as inconclusive. The system can use tested samples with confirmed biopsies will be to access model performance and provide updated training set for incremental learning on the analytical models.

Figure 23:
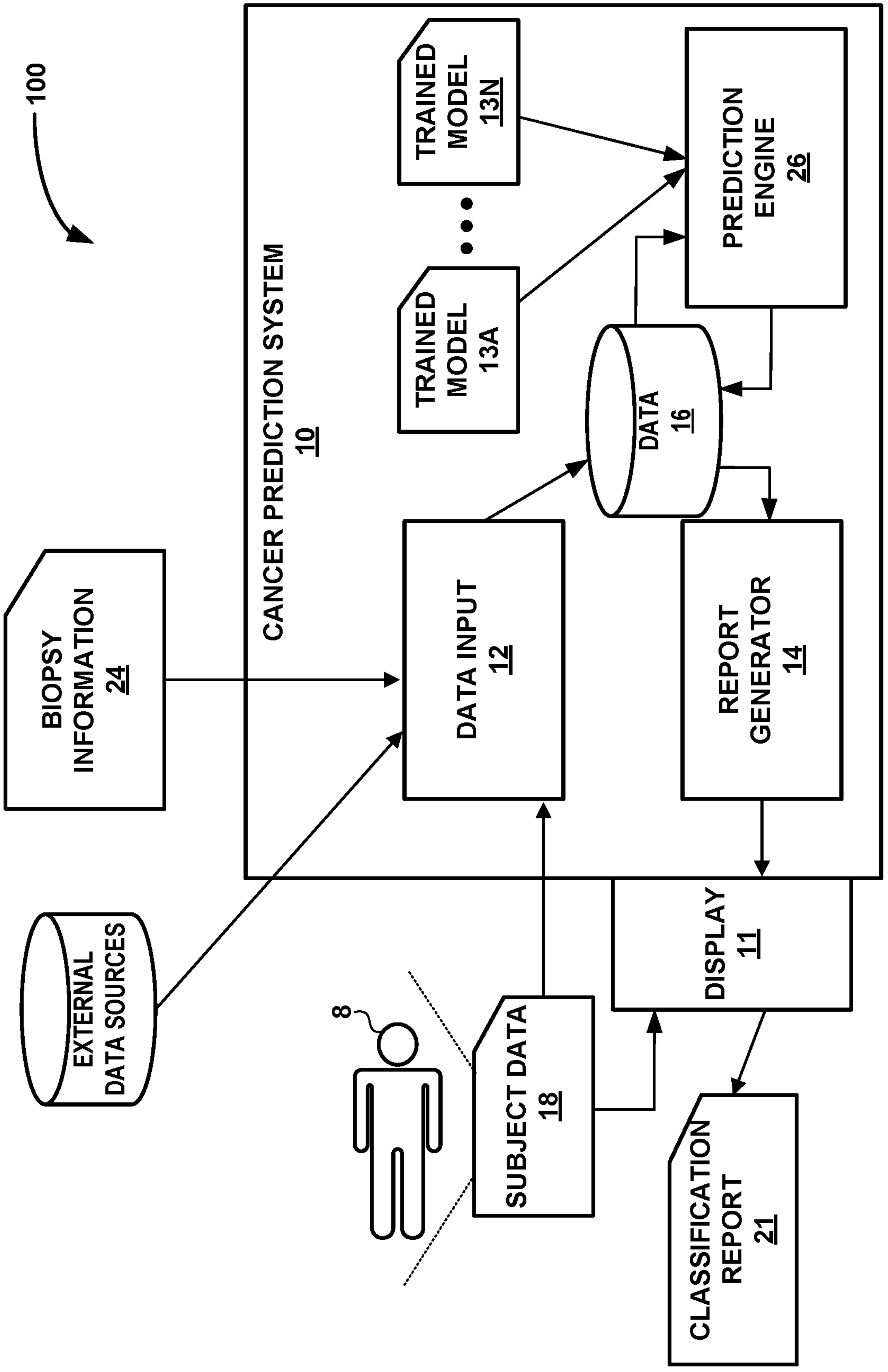
FIG. 23 is a block diagram illustrating an example computing system for predicting cancer risk for one or more subjects configured in accordance with one or more techniques of the present disclosure.

FIG. 23 is a block diagram illustrating an example computing system for predicting cancer risk for one or more subjects configured in accordance with one or more techniques of the present disclosure. As shown in the example of FIG. 23, system 10 may represent a computing device or computing system, such as a mobile computing device (e.g., a smartphone, a tablet computer, a personal digital assistant, and the like), a desktop computing device, a server system, a distributed computing system (e.g., a "cloud" computing system), or any other device capable of receiving patient data 18 and performing the techniques described herein. System 10 may include processing circuitry configured to execute prediction engine 26 or perform any other analysis or calculations described herein.

System 10 may include a data repository (e.g., data 16 and/or external data sources) configured to store a plurality of data features from flow cytometric measurements for a blood sample from a subject 8. The data features and/or flow cytometric measurements may be included in subject data 18 that is received by data input 12 and stored in data 16. Data input 12 may, for example, query subject data 18 (e.g., from a flow cytometer), external data sources such as remote databases or systems, biopsy information 24, or other sources to automatically obtain the data. In addition, or alternatively, data input 12 may receive data manually from one or more users. The processing circuitry (e.g., not shown in FIG. 23 but may be contained by cancer prediction system 10) may be configured to receive the plurality of data features for the blood sample of subject 8, which may be generated by a flow cytometry system (not shown). The processing circuitry may also execute prediction engine 26 configured to apply a plurality of trained analytical models (e.g., trained model 13A and one or more trained model 13N) to at least a respective subset of the plurality of data features for the blood sample of the subject to compute, for each trained analytical model of the plurality of trained analytical models, one classification for the blood sample, wherein the classification is selected from a plurality of classification options comprising at least a HSA classification and a healthy classification.

The processing circuitry (with or without prediction engine 26) may determine that a threshold quantity of trained analytical models resulted in a same one classification for the blood sample, and responsive to determining that the threshold quantity of trained analytical models of the plurality of analytical models resulted in the same one classification for the blood sample, output the same one classification as a final classification for the blood sample from the subject. In some examples, the prediction engine may store the classifications data 16, which may then be obtained by report generator 14 which controls display 11 to present the classification report 21 to a user. In some examples, data input 12 may obtain biopsy information 24 or other data from other external data sources that cancer prediction system 10 may employ to train the trained analytical models 13A and/or 13N or otherwise classify subjects as discussed herein.

In some examples, the plurality of classification options may include the HSA classification, the healthy classification, a splenic hematoma, and a cancer other than HSA. Although these four different classification options, or groups, may be used as described herein for cancer detection, a smaller or larger number of classification options may be employed in other examples. For example, the classification options may be binary such as a high risk of HSA and a low risk of HSA. In other examples, three or more tiers of risk of HSA may be provided based on the number of algorithms indicating HSA for the subject.

In some examples, each of the plurality of trained analytical models (e.g., trained analytical models 13A and 13N), may be applied to the same data features for the subject. In other examples, the respective subset of the plurality of data features is different for at least two trained analytical models of the plurality of trained analytical models used to classify the subject. Prior to classifying unknown samples, prediction engine 26 may be configured to determine, for each trained analytical model of the plurality of trained analytical model, the respective subset of the plurality of data features according to a plurality of statistical scoring methods. In this manner, prediction engine 26 may train one or more analytical models using different sets of data features in order to obtain the data feature combination that improves classification of the subjects.

The plurality of data features to which prediction engine 26 applies each trained analytical model may include at least two flow cytometric measurements from the following: (1) normalized count for Quadrant-1 (Q1)_progenitors (CD34+/c-Kit+); (2) normalized count for Q2_double positive (CD34+/c-Kit+/$\alpha v\beta_3$-integrin+); (3) normalized count for Q3_avb$_3$ ($\alpha_v\beta_3$-integrin+); (4) normalized count for Q3 SS high (high complexity–Side Scatter>100); (5) normalized count for Q3 SS low (low complexity–Side Scatter<100); (6) total $\alpha_v\beta_3$-integrin normalized fluorescence intensity (FI) from negative (Q4) and positive (Q3) populations; (7) relative mean $\alpha_v\beta_3$-integrin FI from negative (Q4) and positive (Q3) populations; (8) relative median $\alpha_v\beta_{3\alpha}$-integrin FI from negative (Q4) and positive (Q3) populations; (9) standard deviation of $\alpha v\beta_3$-integrin FI from negative (Q4) and positive (Q3) populations; (10) relative minimum $\alpha v\beta_3$-integrin FI from negative (Q4) and positive (Q3) populations; and (11) relative maximum $\alpha v\beta_3$-integrin FI from negative (Q4) and positive (Q3) populations. Other data features, or parameters, may be used in other examples. Different trained analytical models may employ a different number of data features as compared to other trained analytical models.

In some examples, the threshold quantity of trained analytical models needed to classify a sample may be a majority of the plurality of trained analytical models. For example, if three analytical models are employed, at least two of the thee analytical models may need to arrive at the same classification for the subject in order to assign that classification to the subject. In this manner, at least three trained analytical models may be applied to the unknown subject data features in some examples. However, in examples with more trained analytical models, the threshold quantity of trained analytical models may be lower, such as two or more models. In other examples, the threshold quantity of trained analytical models may include weights for different analytical models in order to weight more accurate models higher than other models that are less accurate. In addition, or alternatively, prediction engine 26 may apply confidence intervals from each model to give higher weight to classifications from models showing higher confidence in the output classification.

The trained analytical models may include at least two of a Logistic Regression (LR) model, a Linear Discriminant Analysis (LDA) model, a k-nearest neighbors (kNN) model, a Neural Network (NN) model, a Support Vector Machine (SVM) model, a Random Forest (RF) model, a Decision Tree Classifier (Tree) model, an Adaptive Boosting (AdaBoost) model, an Extra Trees Classifier (EXT) model, a Bagging (BAG) model, a Gaussian Naïve Bayes (NB) model, a Stochastic Gradient Boosting (SGB) model, or Deep Learning (DL) model. Prediction engine 26 may also train and select the analytical models for use in prediction. For example, the data repository (e.g., data 16) may be configured to store a plurality of population data features from flow cytometric measurements of a plurality of blood samples from respective subjects that may belong to known groups. Prediction engine 26 may be configured to test a plurality of initial analytical models with the plurality of population data features and determine, for each initial analytical model of the plurality of initial analytical models, a score according to the test. This score may be an average score or other metric indicative of the performance of each different analytical model in classifying the samples. Then, prediction engine 26 may be configured to determine, based on the score for each initial analytical model, a subset of the plurality of initial analytical models for training as the plurality of trained analytical models. This subset of initial analytical models are thus the models that prediction engine 26 applies to the data features of unknown, or unclassified, samples.

Figure 24:
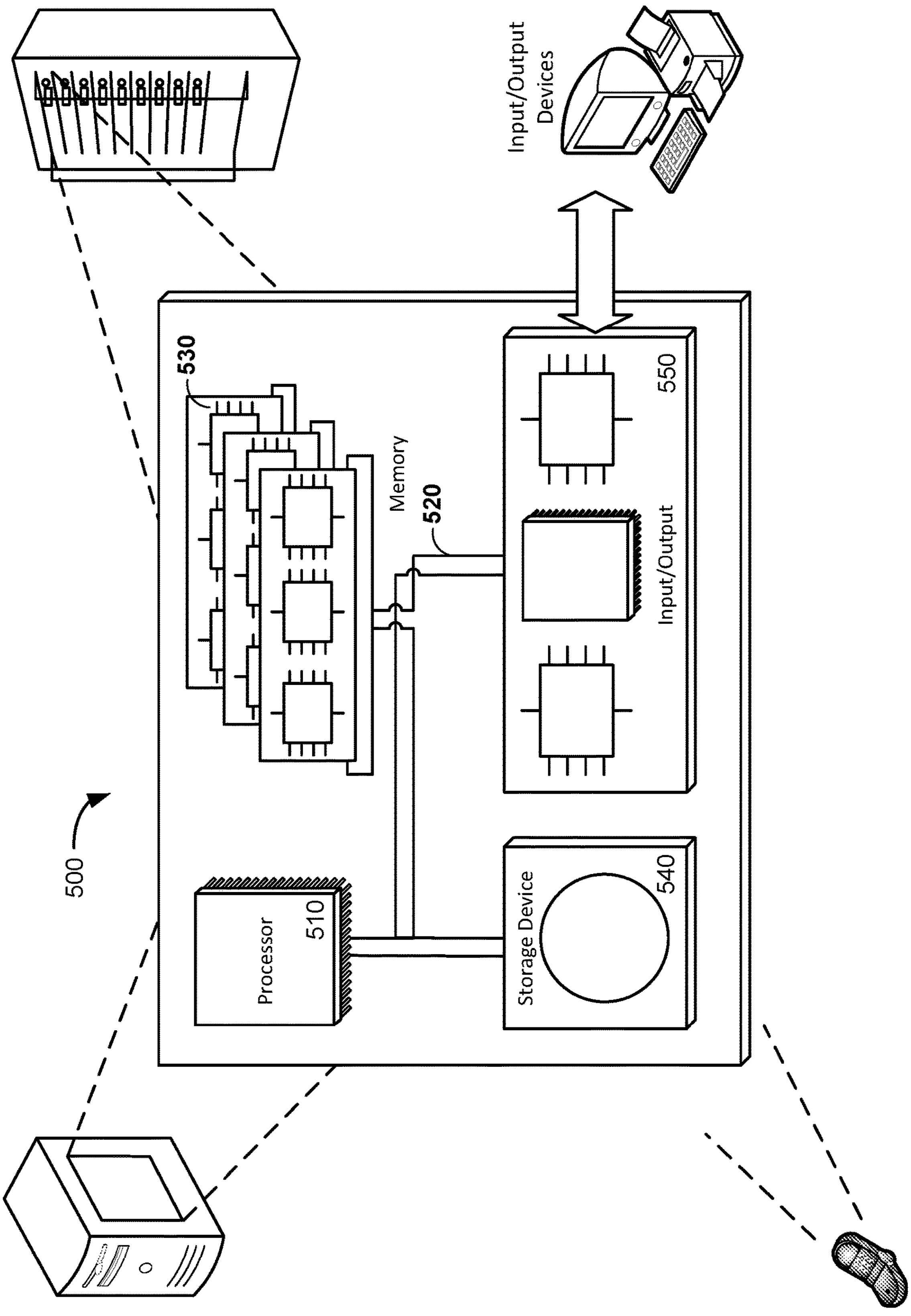
FIG. 24 is a block diagram illustrating an example of various devices that may be configured to implement one or more techniques of the present disclosure.

FIG. 24 is a block diagram illustrating an example of various devices that may be configured to implement one or more techniques of the present disclosure. That is, device 500 of FIG. 24 provides an example implementation for the cancer prediction system 10 of FIG. 23 for predicting cancer risk for subjects. Device 500 may be a mobile device (e.g., a tablet, a personal digital assistant, or other mobile device), a workstation, a computing center, a cluster of servers, or other examples of a computing environment, centrally located or distributed, that is capable of executing the techniques described herein. Any or all of the devices may, for example, implement portions of the techniques described herein for generating and outputting predicted prostate cancer visualizations for display. In some examples, functionality of cancer prediction system 10 may be distributed across multiple computing devices, such as a cloud-based computing system for computing the predicted scores and generating the reports, and a client device, such as a table or mobile phone, for accessing and viewing the reports.

In the example of FIG. 24, computer-implemented device 500 includes a processor 510 (e.g., processing circuitry) that is operable to execute program instructions or software, causing the computer to perform various methods or tasks, such as performing the techniques for generating and/or using analytical models for cancer prediction as described herein. Processor 510 is coupled via bus 520 to a memory 530, which is used to store information such as program instructions and/or other data while the computer is in operation. A storage device 540, such as a hard disk drive, nonvolatile memory, or other non-transient storage device stores information such as program instructions, data files of the multidimensional data and the reduced data set, and other information. The computer also includes various input-output elements 550, including parallel or serial ports, USB, Firewire or IEEE 1394, Ethernet, and other such ports to connect the computer to external devices such a printer, video camera, display device, medical imaging device, surveillance equipment or the like. Other input-output elements include wireless communication interfaces such as Bluetooth, Wi-Fi, and cellular data networks.

The computer itself may be a traditional personal computer, a rack-mount or business computer or server, or any other type of computerized system. The computer, in a further example, may include fewer than all elements listed above, such as a thin client or mobile device having only some of the shown elements. In another example, the computer is distributed among multiple computer systems, such as a distributed server that has many computers working together to provide various functions.

Figure 25:
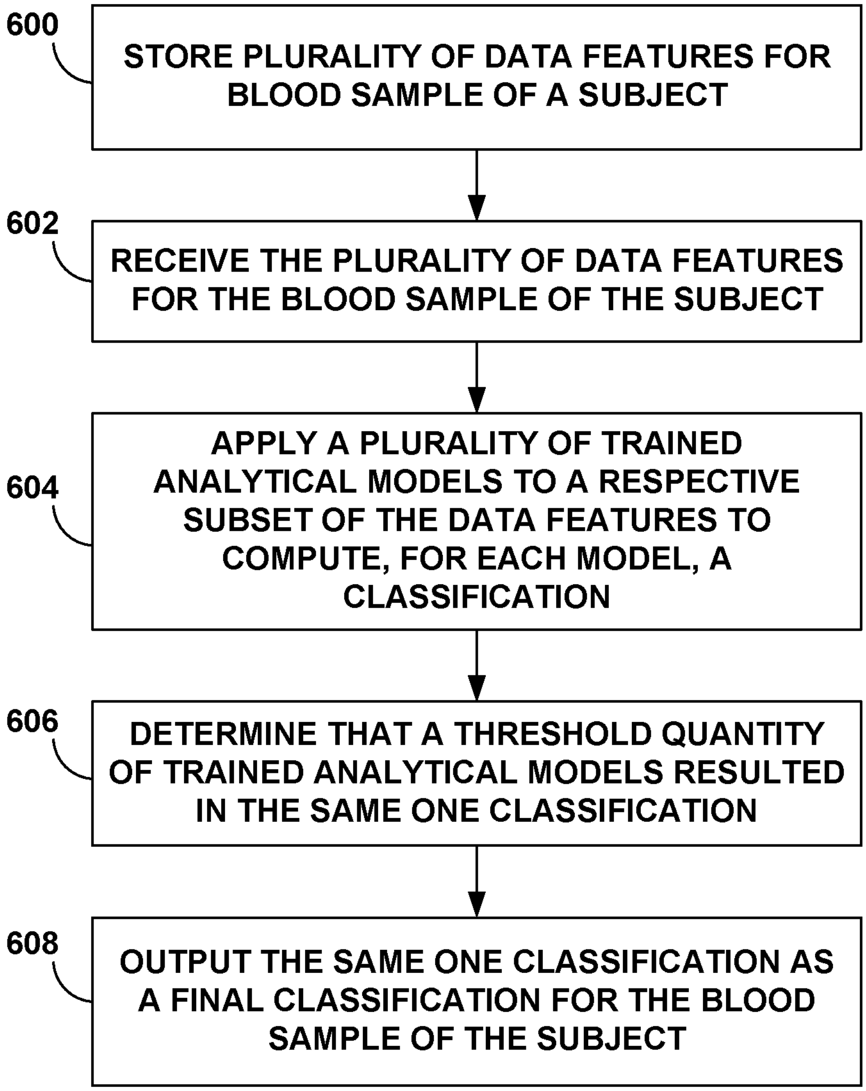
FIG. 25 is a flowchart illustrating example operation in accordance with the present techniques.

FIG. 25 is a flowchart illustrating example operation in accordance with the present techniques. The technique of FIG. 25 may be performed by system 10 as shown in FIG. 23, but other systems described herein may similarly employ these techniques. As shown in the example of FIG. 25, data input 12 may store a plurality of data features from flow cytometric measurements for a blood sample from a subject in data 16, which is a data repository (600). Prediction engine 26, executed by processing circuitry, then receives the plurality of data features for the blood sample of the subject (602) and applies a plurality of trained analytical models to at least a respective subset of the plurality of data features for the blood sample of the subject to compute, for each trained analytical model of the plurality of trained analytical models, one classification for the blood sample (604). The classification may be selected from a plurality of classification options comprising at least a HSA classification and a healthy classification. As discussed above, other classification options may also be available for selection.

Prediction engine 26 then determines that a threshold quantity of trained analytical models resulted in a same one classification for the blood sample (606). Alternatively, prediction engine 26 may determine that the threshold quantity has not resulted in the same classification, which may lead to an inconclusive determination for the subject because none, or too few, of the models were in agreement on the classification. Responsive to determining that the threshold quantity of trained analytical models of the plurality of analytical models resulted in the same one classification for the blood sample, prediction engine 26 outputs the same one classification as a final classification for the blood sample from the subject (608). In some examples, report generator 14 (which may be executed by processing circuitry, may control display 11 to display the final classification, or an inconclusive determination, as a part of the classification report 21 to a user.

The following examples are described herein. Example 1: a method comprising obtaining a plurality of cells from a blood sample of a subject, the plurality of cells comprising at least one of circulating tumor cells or circulating tumor-associated cells; marking the plurality of cells with antibodies that recognize a plurality of markers comprising at least two of $\alpha_v\beta_3$-integrin, hematopoietic progenitor marker CD34, hematopoietic progenitor marker CD117, hyaluronic acid receptor CD44, or panleukocyte marker CD45; obtaining, based on expression of the plurality of markers in the plurality of cells, a plurality of data features for the plurality of cells from the blood sample of the subject; applying a plurality of trained analytical models to at least a respective subset of the plurality of data features for the plurality of cells from the blood sample of the subject; and generating, based on the application of the plurality of trained analytical models to at least the respective subset of the plurality of data features, one classification for the blood sample, wherein the classification is selected from a plurality of classification options comprising at least high risk of HSA classification and a low risk of HSA classification.

Example 2: the method of example 1, wherein the circulating tumor cells comprise HSA cells.

Example 3: the method of any of examples 1 and 2, wherein the circulating tumor-associated cells comprise at least one of activated endothelial cells, platelet-coated leukocytes, or cells mobilized from a pathological vascular niche.

Example 4: the method of any of examples 1 through 3, further comprising: performing flow cytometry on the plurality of cells; and generating, based on the flow cytometry, the plurality of data features.

Example 5: the method of any of examples 1 through 4, wherein the plurality of markers comprise at least one of (a) the $\alpha_v\beta_3$-integrin, the hematopoietic progenitor marker CD34, and the hematopoietic progenitor marker CD117, or (b) the $\alpha_v\beta_3$-integrin and the hyaluronic acid receptor CD44.

Example 6: the method of any of examples 1 through 5, further comprising obtaining the blood sample from the subject.

Example 7: the method of any of examples 1 through 6, further comprising, prior to obtaining the plurality of cells, subjecting the blood sample to hypotonic lysis to eliminate erythrocytes and deplete platelet levels from the blood sample.

Example 8: the method of example 7, wherein obtaining the plurality of cells comprises removing, from the blood sample, at least some T cells, B cells, and myeloid cells.

Example 9: the method of any of examples 1 through 8, wherein the plurality of classification options comprises the high risk of HSA classification, the low risk of HSA classification, a medium risk of HSA classification.

Example 10: the method of any of examples 1 through 9, wherein applying the plurality of trained analytical models comprises executing a prediction engine configured to apply the plurality of trained analytical models to at least the respective subset of the plurality of data features for the blood sample of the subject to compute, for each trained analytical model of the plurality of trained analytical models, the one classification for the blood sample.

Example 11: the method of example 10, further comprising determining that a threshold quantity of trained analytical models resulted in the one classification for the blood sample, wherein generating the one classification comprises, responsive to determining that the threshold quantity of trained analytical models of the plurality of analytical models resulted in the one classification for the blood sample, outputting the one classification as a final classification for the blood sample from the subject.

Example 12: the method of example 11, wherein the threshold quantity of trained analytical models comprises a majority of the plurality of trained analytical models.

Example 13: the method of any of examples 1 through 12, wherein the plurality of trained analytical models comprise at least three analytical models.

Example 14: the method of any of examples 1 through 13, wherein the plurality of trained analytical models comprise at least two of a Logistic Regression (LR) model, a Linear Discriminant Analysis (LDA) model, a k-nearest neighbors (kNN) model, a Neural Network (NN) model, a Support Vector Machine (SVM) model, a Random Forest (RF) model, a Decision Tree Classifier (Tree) model, an Adaptive Boosting (AdaBoost) model, an Extra Trees Classifier (EXT) model, a Bagging (BAG) model, a Gaussian Naïve Bayes (NB) model, a Stochastic Gradient Boosting (SGB) model, or Deep Learning (DL) model.

Example 15: the method of any of examples 1 through 14, wherein the subject comprises a dog.

Example 16, a system configured to perform the methods of any of examples 1 through 15.

Example 17: a system comprising: data repository configured to store a plurality of data features from flow cytometric measurements for a blood sample from a subject; and processing circuitry configured to: receive the plurality of data features for the blood sample of the subject; execute a prediction engine configured to apply a plurality of trained analytical models to at least a respective subset of the plurality of data features for the blood sample of the subject to compute, for each trained analytical model of the plurality of trained analytical models, one classification for the blood sample, wherein the classification is selected from a plurality of classification options comprising at least a HSA classification and a healthy classification; determine that a threshold quantity of trained analytical models resulted in a same one classification for the blood sample; and responsive to determining that the threshold quantity of trained analytical models of the plurality of analytical models resulted in the same one classification for the blood sample, output the same one classification as a final classification for the blood sample from the subject.

Example 18: the system of example 17, wherein the plurality of classification options comprises the HSA classification, the healthy classification, a splenic hematoma, and a cancer other than HSA.

Example 19: the system of any of examples 17 and 18, wherein the respective subset of the plurality of data features is different for at least two trained analytical models of the plurality of trained analytical models.

Example 20: the system of any of examples 17 through 19, wherein the prediction engine is configured to determine, for each trained analytical model of the plurality of trained analytical model, the respective subset of the plurality of data features according to a plurality of statistical scoring methods.

Example 21: the system of any of examples 17 through 20, wherein the plurality of data features comprise at least two flow cytometric measurements from the following: (1) normalized count for Quadrant-1 (Q1)_progenitors (CD34+/c-Kit+); (2) normalized count for Q2_double positive (CD34+/c-Kit+/$\alpha v\beta_3$-integrin+); (3) normalized count for Q3_avb$_3$ ($\alpha v\beta_3$-integrin+); (4) normalized count for Q3 SS high (high complexity–Side Scatter>100); (5) normalized count for Q3 SS low (low complexity–Side Scatter<100); (6) total $\alpha v\beta_3$-integrin normalized fluorescence intensity (FI) from negative (Q4) and positive (Q3) populations; (7) relative mean $\alpha v\beta_3$-integrin FI from negative (Q4) and positive (Q3) populations; (8) relative median $\alpha v\beta_3$-integrin FI from negative (Q4) and positive (Q3) populations; (9) standard deviation of $\alpha v\beta_3$-integrin FI from negative (Q4) and positive (Q3) populations; (10) relative minimum $\alpha v\beta_3$-integrin FI from negative (Q4) and positive (Q3) populations; and (11) relative maximum $\alpha v\beta_3$-integrin FI from negative (Q4) and positive (Q3) populations.

Example 22: the system of any of examples 17 through 21, wherein the threshold quantity of trained analytical models comprises a majority of the plurality of trained analytical models.

Example 23: the system of any of examples 17 through 22, wherein the plurality of trained analytical models comprise at least three analytical models.

Example 24: the system of any of examples 17 through 23, wherein the plurality of trained analytical models comprise at least two of a Logistic Regression (LR) model, a Linear Discriminant Analysis (LDA) model, a k-nearest neighbors (kNN) model, a Neural Network (NN) model, a Support Vector Machine (SVM) model, a Random Forest (RF) model, a Decision Tree Classifier (Tree) model, an Adaptive Boosting (AdaBoost) model, an Extra Trees Classifier (EXT) model, a Bagging (BAG) model, a Gaussian Naïve Bayes (NB) model, a Stochastic Gradient Boosting (SGB) model, or Deep Learning (DL) model.

Example 25: the system of any of examples 17 through 24, wherein: the data repository is configured to store a plurality of population data features from flow cytometric measurements of a plurality of blood samples from respective subjects; and the prediction engine is configured to: test a plurality of initial analytical models with the plurality of population data features; determine, for each initial analytical model of the plurality of initial analytical models, a score according to the test; and determine, based on the score for each initial analytical model, a subset of the plurality of initial analytical models for training as the plurality of trained analytical models.

Example 26: the system of any of examples 17 through 25, wherein one or more of a cloud-based computing platform, a mobile device, a laptop, or a server comprises the processing circuitry.

Example 27: the system of any of examples 17 through 26, further comprising means for performing the functions described herein.

Example 28: a method comprising: storing, by a data repository, a plurality of data features from flow cytometric measurements for a blood sample from a subject; receiving, by processing circuitry, the plurality of data features for the blood sample of the subject; executing, by the processing circuitry, a prediction engine configured to apply a plurality of trained analytical models to at least a respective subset of the plurality of data features for the blood sample of the subject to compute, for each trained analytical model of the plurality of trained analytical models, one classification for the blood sample, wherein the classification is selected from a plurality of classification options comprising at least a HSA classification and a healthy classification; determining, by the processing circuitry, that a threshold quantity of trained analytical models resulted in a same one classification for the blood sample; and responsive to determining that the threshold quantity of trained analytical models of the plurality of analytical models resulted in the same one classification for the blood sample, outputting, by the processing circuitry, the same one classification as a final classification for the blood sample from the subject.

Example 29: a computing system comprising means for performing the method of example 28.

Example 30: a non-transitory computer-readable medium comprising program code for causing a processor to execute the method of example 28.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media, which includes any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable storage medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Further examples are provided in the Appendix attached below and incorporated herein by reference.

What is claimed is:

1. A method comprising:

subjecting a blood sample of a canine subject to hypotonic lysis;

obtaining a plurality of cells from the blood sample after the lysis, the plurality of cells comprising at least one of circulating tumor cells or circulating tumor-associated cells, wherein the circulating tumor cells comprise hemangiosarcoma (HSA) cells, and wherein the circulating tumor-associated cells comprise HSA-associated cells further comprising at least one of activated endothelial cells, platelet-coated leukocytes, or cells mobilized from a pathological vascular niche;

obtaining a plurality of data features for the plurality of cells from the blood sample of the canine subject;

applying each trained machine learning model of at least three a plurality of machine learning models to at least a respective subset of a corresponding plurality of respective subsets of the plurality of data features for the plurality of cells from the blood sample of the canine subject, wherein at least two respective subsets of the corresponding plurality of respective subsets of the plurality of data features are different, and wherein at least two respective subsets of the corresponding plurality of respective subsets of the plurality of data features are the same;

generating, based on the application of each trained machine learning model of the plurality of at least three machine learning models to at least the respective subset of the corresponding plurality of respective subsets of the plurality of data features, a plurality of classifications, each classification corresponding to a respective trained machine learning model of the plurality of at least three trained machine learning models; and outputting, based on a determination that a threshold quantity of trained machine learning models resulted in a same one classification for the blood sample, the same one classification for the blood sample, wherein the classification is selected from a plurality of classification options comprising at least a high risk of hemangiosarcoma HSA classification and a low risk of HSA classification.

2. The method of claim 1, wherein the plurality of cells comprises the circulating tumor cells.

3. The method of claim 1, wherein the plurality of cells comprises the circulating tumor-associated cells.

4. The method of claim 1, further comprising obtaining the blood sample from the canine subject.

5. The method of claim 1, wherein subjecting the blood sample to hypotonic lysis eliminates erythrocytes and depletes platelet levels from the blood sample.

6. The method of claim 5, wherein obtaining the plurality of cells comprises removing, from the blood sample, at least some T cells, B cells, and myeloid cells.

7. The method of claim 1, wherein the plurality of classification options comprises the high risk of HSA classification, the low risk of HSA classification, and a medium risk of HSA classification.

8. The method of claim 1, wherein applying the at least three machine learning models comprises executing, by processing circuitry, a prediction engine configured to apply each machine learning model of the at least three machine learning models to at least the respective subset of the plurality of data features for the blood sample of the canine subject.

9. The method of claim 1, wherein the threshold quantity of trained machine learning models comprises a majority of the at least three trained machine learning models.

10. The method of claim 1, wherein the plurality of trained machine learning models comprise at least two of a Logistic Regression (LR) model, a Linear Discriminant Analysis (LDA) model, a k-nearest neighbors (kNN) model, a Neural Network (NN) model, a Support Vector Machine (SVM) model, a Random Forest (RF) model, a Decision Tree Classifier (Tree) model, an Adaptive Boosting (AdaBoost) model, an Extra Trees Classifier (EXT) model, a Bagging (BAG) model, a Gaussian Naïve Bayes (NB) model, a Stochastic Gradient Boosting (SGB) model, or Deep Learning (DL) model.

11. The method of claim 1, wherein the canine subject comprises a dog.

12. The method of claim 1, further comprising marking the plurality of cells with antibodies that recognize a plurality of markers comprising at least two of $\alpha_v\beta_3$-integrin, hematopoietic progenitor marker CD34, hematopoietic progenitor marker CD117, hyaluronic acid receptor CD44, or panleukocyte marker CD45, and wherein obtaining the plurality of data features comprises obtaining, based on expression of the plurality of markers in the plurality of cells, the plurality of data features.

13. The method of claim 12, further comprising:

performing flow cytometry on the plurality of cells; and generating, based on the flow cytometry, the plurality of data features.

14. The method of claim 12, wherein the plurality of markers comprise at least one of (a) the $\alpha_v\beta_3$-integrin, the hematopoietic progenitor marker CD34, and the hematopoietic progenitor marker CD117, or (b) the $\alpha_v\beta_3$-integrin and the hyaluronic acid receptor CD44.

* * * * *